US007923204B2

(12) United States Patent
Glaab et al.

(10) Patent No.: US 7,923,204 B2
(45) Date of Patent: Apr. 12, 2011

(54) FORWARD MUTATION ASSAY BASED ON 5-FLUOROURACIL RESISTANCE

(75) Inventors: Warren E. Glaab, Doylestown, PA (US); Thomas R. Skopek, Collegeville, PA (US); Katerina Vlasakova, Hatfield, PA (US); Judith E. Miller, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 758 days.

(21) Appl. No.: 10/554,433

(22) PCT Filed: Apr. 22, 2004

(86) PCT No.: PCT/US2004/012330
§ 371 (c)(1),
(2), (4) Date: Oct. 24, 2005

(87) PCT Pub. No.: WO2004/096987
PCT Pub. Date: Nov. 11, 2004

(65) Prior Publication Data
US 2007/0042343 A1 Feb. 22, 2007

Related U.S. Application Data

(60) Provisional application No. 60/465,753, filed on Apr. 26, 2003.

(51) Int. Cl.
*C12Q 1/00* (2006.01)
*C12Q 1/02* (2006.01)
*C12Q 1/18* (2006.01)

(52) U.S. Cl. .................. 435/4; 435/29; 435/32

(58) Field of Classification Search ................... None
See application file for complete search history.

(56) References Cited

U.S. PATENT DOCUMENTS 4,190,495 A 2/1980 Curtiss et al.
4,968,619 A 11/1990 Curtiss et al.
6,344,344 B1 * 2/2002 Kazarinova et al. ............ 435/87

OTHER PUBLICATIONS

McCann et al (Detection of Carcinogens as Mutagens: Bacterial Tester Strains with R Factor Plasmids. PNAS, 1975. 72(3):979-983.*
Genbank: U72482, http://www.ncbi.nlm.nih.gov/nuccore/4335688, Oct. 12, 2005.*
Delmarini et al (Influence of DNA repair on mutation spectra in Salmonella. Mutation Research, 2000. 450:5-17).*
Landis et al (Tolerance of 5-fluorodexyuridie resistance human thymidylate synthases to alteration in active site residues. Nucleic acids Research, 27(18):3702-3711), 1999.*
Tiraby et al (Concomitant expression of *E. coli* cytosine deaminase and uracil phosphoribosyltransferase improves the cytotoxicity of 5-fluorocytosine. FEMS Microbiology Letters, 1998. 167:41-49).*
Ames, B. et al. "Methods for Detecting Carcinogens and Mutagens with the Salmonella/Mammalian-Microsome Mutagenicity Test", Mutation Research, vol. 31, pp. 347-364, 1975.
Skopek, T. et al. "Rate of induced forward mutation at 3 genetic loci in *Salmonella typhimurium*", Mutation Research, vol. 108, pp. 45-56, 1983.
Ames, B. "Carcinogens are Mutagens: Their Detection and Classification", Environmental Health Perspectives, vol. 6, pp. 115-118, 1973.
McCalla, D. et al. "Mutagen Screening with Bacteria: Niridazole and Nitrofurans", Mutation Research, vol. 31, pp. 31-37, 1975.
O'Donovan, G. et al. "Pyrimidine Metabolism in Microorganisms", Bacteriological Reviews, vol. 34, pp. 278-343, 1970.
Anderson, P. et al. "Characterization of the *upp* gene encoding uracil phosphoribosyltransferase of *Escherichia coli* K12", Eur. J. Biochem., vol. 204, pp. 51-56, 1992.
Molloy, A. et al. "Uridine-5'-Monophosphate Pyrophosphorylase Activity from *Escherichia coli*", FEBS Letters, vol. 5, pp. 211-213, 1969.
Glaab, W. et al. "5-Fluorouracil forward mutation assay in *Salmonella*: Determination of mutational target and spontaneous mutational spectra", Mutation Research, vol. 578, pp. 238-246, 2005.
Vlasakova, K. et al. "Induced mutation spectra at the *upp* locus in *Salmonella typhimurium*: Response of the target gene in the FU assay to mechanistically different mutagens", Mutation Research, vol. 578, pp. 225-237, 2005.
Miller, J. et al. "A low volume, high-throughput forward mutation assay in *Salmonella typhimurium* based on fluorouracil resistance", Mutation Research, vol. 578, pp. 210-224, 2005.
Skopek, T. et al. "Relative sensitivities of forward and reverse mutation assays in *Salmonella typhimurium*", Proc. Natl. Acad. Sci. USA, vol. 75, pp. 4465-4469, 1978.

* cited by examiner

*Primary Examiner* — Janet L. Epps-Smith
(74) *Attorney, Agent, or Firm* — Melissa B. Wenk; Sheldon O. Heber

(57) ABSTRACT

Disclosed herein is a novel forward mutation assay based on 5-fluorouracil (5-FU) resistance which utilizes a strain of *Salmonella typhimurium* derived from the Ames strain TA100. More specifically, the invention provides a high throughput alternative to the standard Ames mutation assay for the evaluation of the genotoxicity activity of compounds during an early stage of the drug development process. The invention also identifies the upp locus as a mutational target that is capable of detecting a diverse spectrum of mutagenic events and further describes a *S. typhimurium* tester strain, designated FU100 (his+, rfa, ΔuvrB, pkM101, 5-fluorouridine resistant) for use in the assay of the invention.

18 Claims, 6 Drawing Sheets

```
gggacaggtcattcacccttaaaattgctaatattcaaacggttgttagcctttatcgcc
tgtttcaacgtgagtgatttatactcacttttccgctatcagcgcttttggttgatccag
gtcaagcatacattgtgttgcgtcagagaggaaaagcggtataatccggcgatttttttt
gtggttgccagtcatctgaggataggagaagagtatgaagatcgtggaagtcaaacaccc
actcgtcaaacacaagctgggtctgatgcgtgaaaacgacattagcactaaacgctttcg
tgaactcgcctcagaagtaggcagcctgctgacgtatgaagcgacagccgacctggaaac
ggaaaaagtcaccatcgaaggctggaatggcccggtggaaatcgaccagatcaaaggtaa
aaaaattaccgttgtgccgattctgcgcgcgggtctgggtatgatggaaggcgttctgga
aaatgtaccgagcgcgcgtatcagcgtagtcgggatgtaccgtaacgaagagacgcttga
gccagtaccttatttccagaaactggtatcgaacattgatgagcgcatggcgctgatcgt
cgaccgatgctggcgactggcggttctgtcatcgcgaccatcgacctgctgaaaaaagc
aggctgtagcagcattaaggtgctggtgctggtcgccgcgccggaaggcattgcggcgct
ggaaaaagcgcacccggacgttgaactgtacaccgcctctatcgatcaggggcttaacga
gcacggatacattattccggggcttggcgatgccggcgataagattttggtaccaaata
agtgaataaataattaaaagccgactttaagagtcggcttttttttgaataaaaccactc
ataacaaacacacttagaggaaaacactatgacgcgccgtgctatcggggtgagtgaaag
accgccgcttttacagacaatcccgcttagtttacagcacctttttcgccatgtttggcgc
gaccgtgctggtgccagttctgtttcatatcaatcccgcgacggtgctgctgtttaacgg
tatcggaacgttgctgtatctctttatctgcaaaggtaaaattcctgcctacctcggatc
gagctttgccttatttccccggtattactgttgttgccgctgggttatgaagtggcgct
gggcggttttattatgtgcggcgtgttgttctgtctggtctctttcatcgttaaaaaagc
gggcaccggctggctggatgtgatgttcccgcctgcggcaatgggcgcaatcgttgccgt
catcggtctggagctggctggcgtcgcggcgggatggccggattactgcctgcgcaagg
gcagtcgccggacacgaaaacaattatcatctccatggtcacgctggcggtgacggtgtt
cggctccgtactgtttcgcggtttcctggcgatcattccgattttgatcggcgtgctggc
gggctatgcgctgtcattcgcgctgggggtggtcgataccacgccgattgcccaggcgca
ctggtttgcgctgccgaccttctatacgccgcgttttgaatggttcgcgatcctgacgat
tctgcccgcggcgttggtcgtgatcgccgagcatgtcggtcatctggtggtgacggcgaa
tatcgtcaaaaaagatttagtgcgcgatcccggtttgcaccgctcgatgttcgctaacgg
actgtcgacgatcatttccggtttcttcggctccacgccgaataccacctatggggaaaa
tattggcgtcatggcgatcacccgcgtttacagtacctgggttatcggcggcgcggcgat
tttcgccattctgctttcctgcgttggcaaactggcggcggcgattcaagattatcccgt
tacccgtgatggcggcgtctcgctgctgttgtacggcgttatcggcgcgtcggggattcg
cgtcttgatcgaatcgaaagtcgactacaacaaagcgcaaaacctgatcctcacctcggt
gatttgatcatcggcgtgagcggcgcgaaagtgcatatcggcgcggcagaattgaaagg
gatggcgctggcgaccatcgtcgggatttgcctgagcctgatttttaaactgattagcct
gttgcgtccggaagaagtggtactggaggcaaatgatgcggagcccccgcatcagtaacg
ggttgccgggcagcgatgctgcccggttctatctcacgggaattatgtggtaaactcagc
gcgatttatgtcatcctggggttgaggtatctctgaacacaccggcacagctctctttgc
cactttatcttcctgacgacgaaactttcgcaagtttctggccgggggataacgcctctc
tactggccgcgttacaaaacgtgttgcgccaggaacatagtggatatatctacctttggg
cgcgtgaaggcgcgggccgcagccatttactgcacgccgcctgtgctgaactgtcgcagc
2520
```

Fig. 1

MKIVEVKHPLVKHKLGLMRENDISTKRFRELASEVGSLLTYE
ATADLETEKVTIEGWNGPVEIDQIKGKKITVVPILRAGLGMM
EGVLENVPSARISVVGMYRNEETLEPVPYFQKLVSNIDERMA
LIVDPMLATGGSVIATIDLLKKAGCSSIKVLVLVAAPEGIAA
LEKAHPDVELYTASIDQGLNEHGYIIPGLGDAGDKIFGTK

Fig. 2

MTRRAIGVSERPPLLQTIPLSLQHLFAMFGATVLVPVLFHIN
PATVLLFNGIGTLLYLFICKGKIPAYLGSSFAFISPVLLLP
LGYEVALGGFIMCGVLFCLVSFIVKKAGTGWLDVMFPPAAMG
AIVAVIGLELAGVAAGMAGLLPAQGQSPDTKTIIISMVTLAV
TVFGSVLFRGFLAIIPILIGVLAGYALSFALGVVDTTPIAQA
HWFALPTFYTPRFEWFAILTILPAALVVIAEHVGHLVVTANI
VKKDLVRDPGLHRSMFANGLSTIISGFFGSTPNTTYGENIGV
MAITRVYSTWVIGGAAIFAILLSCVGKLAAAIQDYPVTRDGG
VSLLLYGVIGASGIRVLIESKVDYNKAQNLILTSVILIIGVS
GAKVHIGAAELKGMALATIVGICLSLIFKLISLLRPEEVVLE
ANDAEPPHQ

Fig. 3

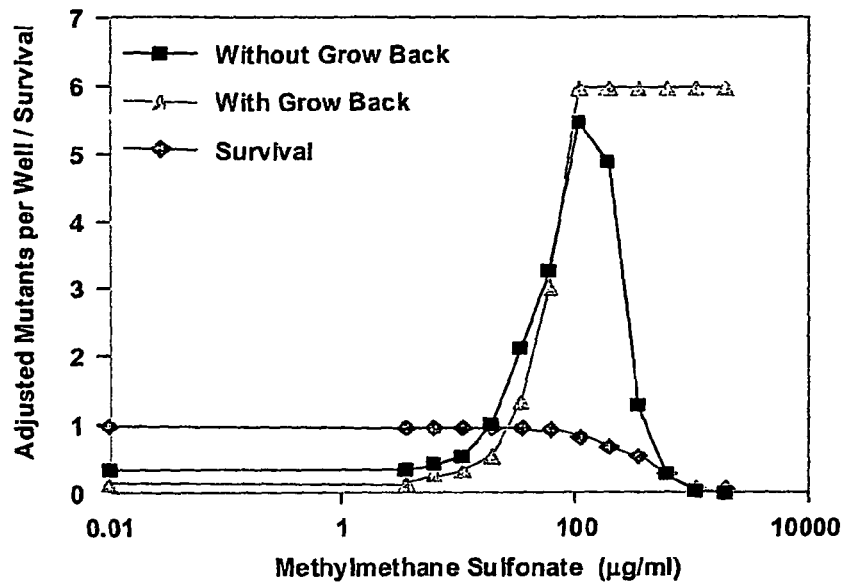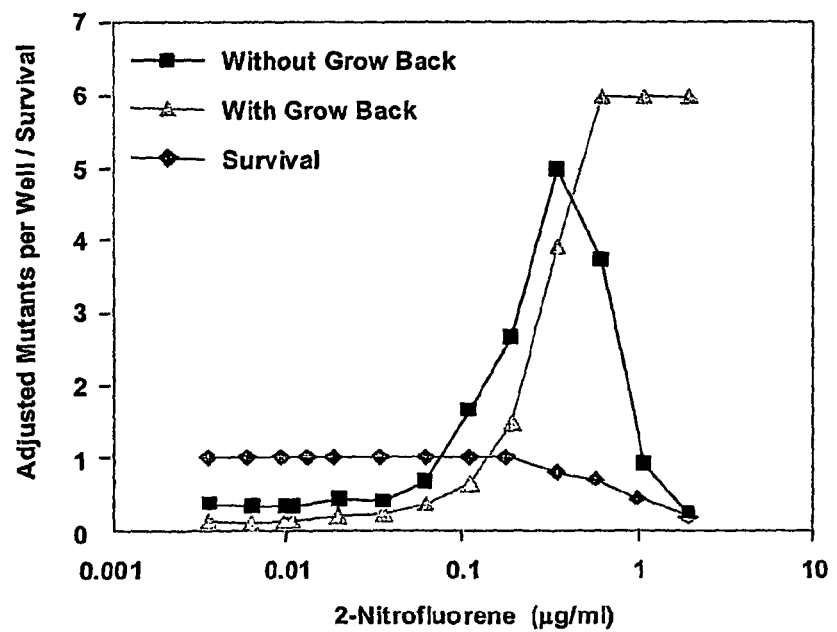
Fig. 5

SEQUENCE LISTING

<160> NUMBER OF SEQ ID NOS: 20

<210> SEQ ID NO 1
<211> LENGTH: 2520
<212> TYPE: DNA
<213> ORGANISM: Salmonella typhimurium

<400> SEQUENCE: 1

```
gggacaggtc attcaccctt aaaattgcta atattcaaac ggttgttagc ctttatcgcc      60
tgtttcaacg tgagtgattt atactcactt ttccgctatc agcgcttttg gttgatccag     120
gtcaagcata cattgtgttg cgtcagagag gaaaagcggt ataatccggc gatttttttt     180
gtggttgcca gtcatctgag gataggagaa gagtatgaag atcgtggaag tcaaacaccc     240
actcgtcaaa cacaagctgg gtctgatgcg tgaaaacgac attagcacta aacgctttcg     300
tgaactcgcc tcagaagtag gcagcctgct gacgtatgaa gcgacagccg acctggaaac     360
ggaaaaagtc accatcgaag gctggaatgg cccggtggaa atcgaccaga tcaaaggtaa     420
aaaaattacc gttgtgccga ttctgcgcgc gggtctgggt atgatggaag cgttctggga     480
aaatgtaccg agcgcgcgta tcagcgtagt cgggatgtac cgtaacgaag agacgcttga     540
gccagtacct tatttccaga aactggtatc gaacattgat gagcgcatgg cgctgatcgt     600
cgacccgatg ctggcgactg gcggttctgt catcgcgacc atcgacctgc tgaaaaaagc     660
aggctgtagc agcattaagg tgctggtgct ggtcgccgcg ccggaaggca ttgcggcgct     720
ggaaaaagcg cacccggacg ttgaactgta caccgcctct atcgatcagg gcttaacga      780
gcacggatac attattccgg ggcttggcga tgccggcgat aagattttg gtaccaaata     840
agtgaataaa taattaaaag ccgactttaa gagtcggctt tttttgaat aaaaccactc      900
ataacaaaca cacttagagg aaaacactat gacgcgccgt gctatcgggg tgagtgaaag     960
accgccgctt ttacagacaa tcccgcttag tttacagcac cttttcgcca tgtttggcgc    1020
gaccgtgctg gtgccagttc tgtttcatat caatcccgcg acggtgctgc tgtttaacgg    1080
tatcggaacg ttgctgtatc tctttatctg caaaggtaaa attcctgcct acctcggatc    1140
gagctttgcc tttatttccc cggtattact gttgttgccg ctgggttatg aagtggcgct    1200
gggcggtttt attatgtgcg gcgtgttgtt ctgtctggtc tctttcatcg ttaaaaaagc    1260
gggcaccggc tggctggatg tgatgttccc gcctgcggca atgggcgcaa tcgttgccgt    1320
catcggtctg gagctggctg gcgtcgcggc ggggatggcc ggattactgc ctgcgcaagg    1380
gcagtcgccg gacacgaaaa caattatcat ctccatggtc acgctggcgg tgacggtgtt    1440
cggctccgta ctgtttcgcg gtttcctggc gatcattccg attttgatcg gcgtgctggc    1500
gggctatgcg ctgtcattcg cgctgggggt ggtcgatacc acgccgattg cccaggcgca    1560
ctggtttgcg ctgccgacct tctatacgcc gcgttttgaa tggttcgcga tcctgacgat    1620
tctgcccgcg gcgttggtcg tgatcgccga gcatgtcggt catctggtgg tgacggcgaa    1680
tatcgtcaaa aaagatttag tgcgcgatcc cggtttgcac cgctcgatgt tcgctaacgg    1740
actgtcgacg atcatttccg gtttcttcgg ctccacgccg aataccacct atgggaaaaa    1800
tattggcgtc atggcgatca cccgcgttta cagtacctgg gttatcggcg gcgcggcgat    1860
tttcgccatt ctgctttcct gcgttggcaa actggcggcg gcgattcaga ttatcccgtt    1920
acccgtgatg ggcggcgtct cgctgctgtt gtacggcgtt atcggcgcgt cggggattcg    1980
cgtcttgatc gaatcgaaag tcgactacaa caaagcgcaa aacctgatcc tcacctcggt    2040
```

```
gattttgatc atcggcgtga gcggcgcgaa agtgcatatc ggcgcggcag aattgaaagg    2100
gatggcgctg gcgaccatcg tcgggatttg cctgagcctg attttttaaac tgattagcct    2160 gttgcgtccg gaagaagtgg tactggaggc aaatgatgcg gagcccccgc atcagtaacg    2220
ggttgccggg cagcgatgct gcccggttct atctcacggg aattatgtgg taaactcagc    2280
gcgattttat gtcatcctgg gttgaggtat ctctgaacac accggcacag ctctctttgc    2340
cactttatct tcctgacgac gaaactttcg caagtttctg gccggggat aacgcctctc    2400 tactggccgc gttacaaaac gtgttgcgcc aggaacatag tggatatatc tacctttggg    2460
cgcgtgaagg cgcgggccgc agccatttac tgcacgccgc ctgtgctgaa ctgtcgcagc    2520
```

<210> SEQ ID NO 2
<211> LENGTH: 208
<212> TYPE: PRT
<213> ORGANISM: Salmonella typhimurium

<400> SEQUENCE: 2

```
Met Lys Ile Val Glu Val Lys His Pro Leu Val Lys His Lys Leu Gly
 1               5                  10                  15

Leu Met Arg Glu Asn Asp Ile Ser Thr Lys Arg Phe Arg Glu Leu Ala
            20                  25                  30

Ser Glu Val Gly Ser Leu Leu Thr Tyr Glu Ala Thr Ala Asp Leu Glu
        35                  40                  45

Thr Glu Lys Val Thr Ile Glu Gly Trp Asn Gly Pro Val Glu Ile Asp
    50                  55                  60

Gln Ile Lys Gly Lys Lys Ile Thr Val Val Pro Ile Leu Arg Ala Gly
65                  70                  75                  80

Leu Gly Met Met Glu Gly Val Leu Glu Asn Val Pro Ser Ala Arg Ile
                85                  90                  95

Ser Val Val Gly Met Tyr Arg Asn Glu Glu Thr Leu Glu Pro Val Pro
           100                 105                 110

Tyr Phe Gln Lys Leu Val Ser Asn Ile Asp Glu Arg Met Ala Leu Ile
       115                 120                 125

Val Asp Pro Met Leu Ala Thr Gly Gly Ser Val Ile Ala Thr Ile Asp
   130                 135                 140

Leu Leu Lys Lys Ala Gly Cys Ser Ser Ile Lys Val Leu Val Leu Val
145                 150                 155                 160

Ala Ala Pro Glu Gly Ile Ala Ala Leu Glu Lys Ala His Pro Asp Val
                165                 170                 175

Glu Leu Tyr Thr Ala Ser Ile Asp Gln Gly Leu Asn Glu His Gly Tyr
            180                 185                 190

Ile Ile Pro Gly Leu Gly Asp Ala Gly Asp Lys Ile Phe Gly Thr Lys
        195                 200                 205
```

<210> SEQ ID NO 3
<211> LENGTH: 429
<212> TYPE: PRT
<213> ORGANISM: Salmonella typhimurium

<400> SEQUENCE: 3

```
Met Thr Arg Arg Ala Ile Gly Val Ser Glu Arg Pro Pro Leu Leu Gln
 1               5                  10                  15

Thr Ile Pro Leu Ser Leu Gln His Leu Phe Ala Met Phe Gly Ala Thr
            20                  25                  30

Val Leu Val Pro Val Leu Phe His Ile Asn Pro Ala Thr Val Leu Leu
        35                  40                  45
```

-continued

```
Phe Asn Gly Ile Gly Thr Leu Leu Tyr Leu Phe Ile Cys Lys Gly Lys
     50                  55                  60

Ile Pro Ala Tyr Leu Gly Ser Ser Phe Ala Phe Ile Ser Pro Val Leu
 65                  70                  75                  80

Leu Leu Leu Pro Leu Gly Tyr Glu Val Ala Leu Gly Gly Phe Ile Met
                 85                  90                  95

Cys Gly Val Leu Phe Cys Leu Val Ser Phe Ile Val Lys Lys Ala Gly
                100                 105                 110

Thr Gly Trp Leu Asp Val Met Phe Pro Pro Ala Ala Met Gly Ala Ile
            115                 120                 125

Val Ala Val Ile Gly Leu Glu Leu Ala Gly Val Ala Ala Gly Met Ala
        130                 135                 140

Gly Leu Leu Pro Ala Gln Gly Gln Ser Pro Asp Thr Lys Thr Ile Ile
145                 150                 155                 160

Ile Ser Met Val Thr Leu Ala Val Thr Val Phe Gly Ser Val Leu Phe
                165                 170                 175

Arg Gly Phe Leu Ala Ile Ile Pro Ile Leu Ile Gly Val Leu Ala Gly
                180                 185                 190

Tyr Ala Leu Ser Phe Ala Leu Gly Val Val Asp Thr Thr Pro Ile Ala
            195                 200                 205

Gln Ala His Trp Phe Ala Leu Pro Thr Phe Tyr Thr Pro Arg Phe Glu
        210                 215                 220

Trp Phe Ala Ile Leu Thr Ile Leu Pro Ala Ala Leu Val Val Ile Ala
225                 230                 235                 240

Glu His Val Gly His Leu Val Val Thr Ala Asn Ile Val Lys Lys Asp
                245                 250                 255

Leu Val Arg Asp Pro Gly Leu His Arg Ser Met Phe Ala Asn Gly Leu
                260                 265                 270

Ser Thr Ile Ile Ser Gly Phe Phe Gly Ser Thr Pro Asn Thr Thr Tyr
            275                 280                 285

Gly Glu Asn Ile Gly Val Met Ala Ile Thr Arg Val Tyr Ser Thr Trp
        290                 295                 300

Val Ile Gly Gly Ala Ala Ile Phe Ala Ile Leu Leu Ser Cys Val Gly
305                 310                 315                 320

Lys Leu Ala Ala Ala Ile Gln Ile Ile Pro Leu Pro Val Met Gly Gly
                325                 330                 335

Val Ser Leu Leu Leu Tyr Gly Val Ile Gly Ala Ser Gly Ile Arg Val
            340                 345                 350

Leu Ile Glu Ser Lys Val Asp Tyr Asn Lys Ala Gln Asn Leu Ile Leu
        355                 360                 365

Thr Ser Val Ile Leu Ile Ile Gly Val Ser Gly Ala Lys Val His Ile
    370                 375                 380

Gly Ala Ala Glu Leu Lys Gly Met Ala Leu Thr Ile Val Gly Ile
385                 390                 395                 400

Cys Leu Ser Leu Ile Phe Lys Leu Ile Ser Leu Leu Arg Pro Glu Glu
                405                 410                 415

Val Val Leu Glu Ala Asn Asp Ala Glu Pro Pro His Gln
            420                 425
```

<210> SEQ ID NO 4
<211> LENGTH: 627
<212> TYPE: DNA
<213> ORGANISM: Salmonella typhimurium

<400> SEQUENCE: 4

-continued

```
atgaagatcg tggaagtcaa acacccactc gtcaaacaca agctgggtct gatgcgtgaa      60
aacgacatta gcactaaacg ctttcgtgaa ctcgcctcag aagtaggcag cctgctgacg     120
tatgaagcga cagccgacct ggaaacggaa aaagtcacca tcgaaggctg aatggcccg      180
gtggaaatcg accagatcaa aggtaaaaaa attaccgttg tgccgattct gcgcgcgggt     240
ctgggtatga tggaaggcgt tctggaaaat gtaccgagcg cgcgtatcag cgtagtcggg     300
atgtaccgta acgaagagac gcttgagcca gtaccttatt ccagaaaact ggtatcgaac     360
attgatgagc gcatggcgct gatcgtcgac ccgatgctgg cgactggcgg ttctgtcatc     420
gcgaccatcg acctgctgaa aaagcaggc tgtagcagca ttaaggtgct ggtgctggtc      480
gccgcgccgg aaggcattgc ggcgctggaa aaagcgcacc cggacgttga actgtacacc     540
gcctctatcg atcaggggct taacgagcac ggatacatta ttccggggct tggcgatgcc     600
ggcgataaga ttttggtac caaataa                                          627
```

\<210\> SEQ ID NO 5
\<211\> LENGTH: 1290
\<212\> TYPE: DNA
\<213\> ORGANISM: Salmonella typhimurium

\<400\> SEQUENCE: 5

```
atgacgcgcc gtgctatcgg ggtgagtgaa agaccgccgc ttttacagac aatcccgctt      60
agtttacagc accttttcgc catgtttggc gcgaccgtgc tggtgccagt tctgtttcat     120
atcaatcccg cgacggtgct gctgtttaac ggtatcggaa cgttgctgta tctctttatc     180
tgcaaaggta aaattcctgc ctacctcgga tcgagctttg cctttatttc cccggtatta     240
ctgttgttgc cgctgggtta tgaagtggcg ctgggcggtt ttattatgtg cggcgtgttg     300
ttctgtctgg tctcttttcat cgttaaaaaa gcgggcaccg gctggctgga tgtgatgttc     360
ccgcctgcgg caatgggcgc aatcgttgcc gtcatcggtc tggagctggc tggcgtcgcg     420
gcggggatgg ccggattact gcctgcgcaa gggcagtcgc cggacacgaa acaattatc     480
atctccatgg tcacgctggc ggtgacggtg ttcggctccg tactgtttcg cggtttcctg     540
gcgatcattc cgattttgat cggcgtgctg gcgggctatg cgctgtcatt cgcgctgggg     600
gtggtcgata ccacgccgat tgcccaggcg cactggtttg cgctgccgac cttctatacg     660
ccgcgttttg aatggttcgc gatcctgacg attctgcccg cggcgttggt cgtgatcgcc     720
gagcatgtcg gtcatctggt ggtgacggcg aatatcgtca aaaaagattt agtgcgcgat     780
cccggttttgc accgctcgat gttcgctaac ggactgtcga cgatcatttc cggtttcttc     840
ggctccacgc cgaataccac ctatgggaa atattggcg tcatggcgat caccgcgtt      900
tacagtacct gggttatcgg cggcgcggcg attttcgcca ttctgctttc ctgcgttggc     960
aaactggcgg cggcgattca gattatcccg ttacccgtga tgggcggcgt ctcgctgctg    1020
ttgtacggcg ttatcggcgc gtcggggatt cgcgtcttga tcgaatcgaa agtcgactac    1080
aacaaagcgc aaaacctgat cctcacctcg gtgattttga tcatcggcgt gagcggcgcg    1140
aaagtgcata tcggcgcggc agaattgaaa gggatggcgc tggcgaccat cgtcgggatt    1200
tgcctgagcc tgattttaa actgattagc ctgttgcgtc cggaagaagt ggtactggag    1260
gcaaatgatg cggagccccc gcatcagtaa                                    1290
```

\<210\> SEQ ID NO 6
\<211\> LENGTH: 21
\<212\> TYPE: DNA
\<213\> ORGANISM: Artificial Sequence
\<220\> FEATURE:

<223> OTHER INFORMATION: Oligonucleotide

<400> SEQUENCE: 6
tttgtggctg cccctcaaag g                                    21

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide

<400> SEQUENCE: 7
aaaagccgac tcttaaagtc ggctt                                25

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide

<400> SEQUENCE: 8
tttgtggttg ccagtcatct gagg                                 24

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide

<400> SEQUENCE: 9
atccaggtca agcatacatt gtgttg                               26

<210> SEQ ID NO 10
<211> LENGTH: 26
<212> TYPE: DNA
<213> ORGANISM: Artificial Sequence
<220> FEATURE:
<223> OTHER INFORMATION: Oligonucleotide

<400> SEQUENCE: 10
aggatatcca gcacttggtt tacgac                               26

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide

<400> SEQUENCE: 11
ctggatcgcg cagcagatct ttttt                                25

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide

<400> SEQUENCE: 12
ataagccgga attttccctt t                                    21

<210> SEQ ID NO 13

```
<211> LENGTH: 26
<212> TYPE: DNA
<213> ORGANISM: Artificial Sequence
<220> FEATURE:
<223> OTHER INFORMATION: Oligonucleotide

<400> SEQUENCE: 13
ccccgctttc ttcacgataa aagaaa                                              26

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide

<400> SEQUENCE: 14
aaaccactca taacaaacac acttag                                              26

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

<400> SEQUENCE: 15
cggtgttcgg ctccgtactg t                                                   21

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
cctcaaccag gatttcacaa a                                                   21

<210> SEQ ID NO 17
<211> LENGTH: 23
<212> TYPE: DNA
<213> ORGANISM: Artificial Sequence
<220> FEATURE:
<223> OTHER INFORMATION: Oligonucleotide

<400> SEQUENCE: 17
gccagtaaag aggagttatc ccc                                                 23

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide

<400> SEQUENCE: 18
cggaacaaac caggtgcgtt t                                                   21

<210> SEQ ID NO 19
<211> LENGTH: 26
<212> TYPE: DNA
<213> ORGANISM: Artificial Sequence
<220> FEATURE:
<223> OTHER INFORMATION: Oligonucleotide

<400> SEQUENCE: 19
```

```
atccaggtca agcatacatt gtgttg                                          26

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide

<400> SEQUENCE: 20
cgatagcacg gcgcgtcat                                                  19
```

FORWARD MUTATION ASSAY BASED ON 5-FLUOROURACIL RESISTANCE

CROSS-REFERENCE TO RELATED APPLICATIONS

The present application claims the benefit of U.S. Provisional Application No. 60/465,753, filed Apr. 26, 2003, hereby incorporated by reference herein.

This application is related to U.S. Provisional Application No. 60/325,128, filed on Sep. 26, 2001, and its corresponding International PCT Application No. PCT/US02130435, filed on Sep. 25, 2002, each of which is incorporated by reference herein its entirety.

FIELD OF THE INVENTION

The present invention relates to a novel forward mutation assay which utilizes the microbial upp gene as a mutational target. The assay of the invention is amenable to both automation and high throughput format thereby making it feasible to use it at an early stage of drug development.

BACKGROUND OF THE INVENTION

Regulatory agencies throughout the world routinely require data on the toxicity of new drugs as a part of the safely evaluation process. The primary objective of the safety evaluation process is to collect information that is indicative of whether the benefits of a using a potential new pharmaceutical compound (e.g., test compound) as a therapeutic agent outweighs the risks and side effects associated with its use. Today, it is not possible to register a new drug without providing information regarding its genotoxic (i.e., mutagenic or carcinogenic) potential.

Although no specific tests are mandated, there is a consensus that recommends the use of a standard four-test battery including: a gene mutation assay in bacteria; an in vitro test for chromosome abberations in mammalian cells; an in vitro test for gene mutation in eukaryotic cells; and an in vivo test for genetic damage. Based on the observation of Dr. Bruce Ames and his colleagues that most carcinogens are also mutagens, numerous test systems (e.g., prokaryotic and eukaryotic) have been developed over the past several years for the purpose of evaluating the genotoxic activity of pharmaceutical compounds and/or their reactive metabolites in various in vitro assays. More specifically, determination of the mutagenic potential of test compounds have historically involved the use of microbial mutation assays, particularly *Salmonella* reversion assays (Ames, B. N., et al., (1975) *Mutation Res.* 31:347-363).

While it is recognized that a drug or new chemical entity can be toxic at different levels, drug-induced mutagenesis of DNA (genotoxicity) underlies many decisions to stop the development of candidate drugs. Generally speaking, genotoxicity can take the form of gene mutation, structural chromosomal abberations, recombination and numerical changes. The standard Ames Assay, which is a cornerstone in the field of toxicology, utilizes several different tester strains, each with a distinct mutation (e.g., transition, frameshift etc.) in one of the genes comprising the histidine (his) biosynthetic operon (Ames, B. N., et al., (1975) *Mutation Res.* 31:347-363). The detection of revertant (i.e., mutant) bacteria in test samples that are capable of growth in the absence of histidine indicates that the compound under evaluation is characterized by genotoxic (i.e. mutagenic) activity. The Ames Assay is capable of detecting several different types of mutations (genetic damage) which may occur in one or more of the tester strains. As mentioned above, the practice of using an in vitro bacterial assay to evaluate the genotoxic activity of drug candidates is based on the prediction that a substance that is mutagenic in a bacterium is likely to be carcinogenic in laboratory animals, and by extension may be carcinogenic or mutagenic to humans. An extensive database containing the results of toxicity data obtained in a traditional bacterial reverse mutation test has been established (McCann, J., et al., (1975) *Proc. Natl. Acad. Sci. USA* 72:5135-9). Generally speaking, the Ames Assay detects the genotoxic activity of carcinogenic/mutagenic compounds belonging to diverse chemical classes with an efficiency of about 80%.

In practice, the Ames Assay is relatively cumbersome to perform because multiple tester strains are necessary due to the fact that chemical mutagens are specific to the type of DNA alteration that they can affect. The standard plate assay utilizes multiple 100-mm dishes and consumes a relatively large amount of compound (i.e., hundreds of milligrams to gram quantities) and can cost from $4000-$5000 per sample.

The requirement for relatively large amounts of compound is also attributed to the fact that in order to increase the probability of identifying DNA-reactive (i.e., genotoxic) compounds, the toxicity of each compound being evaluated is typically tested at several doses on multiple genetically distinct tester strains. Thus, it is understandable that under the traditional paradigm of drug discovery, the Ames reversion test is routinely performed relatively late in the drug discovery process.

Recent advances in the fields of combinatorial chemistry and high throughput screening has brought the drug discovery process to a point where large numbers of molecules with great diversity can be readily synthesized and evaluated for biological activity. The incorporation of combinatorial chemistry into the drug development process has left some companies with a backlog of hundreds of thousands of compounds, many of which may be available in limited quantities, waiting to be tested as therapeutic agents. Because the financial investment in drug discovery increases exponentially as a compound progresses from initial discovery, through development and registration, there is a heightened need for more efficient means of evaluating the safety of new chemical entities at a relatively early stage of the drug development process.

The development of a high throughput genotoxicity assay could potentially save significant amounts of time and money by allowing investigators to eliminate compounds with genotoxic activity at an early stage of the drug development process. Thus, the development of a sensitive, bacterial genotoxic assay with by low compound requirements, that is amenable to automation, and which facilitates high throughput screening formats addresses an unmet need in the field of genetic toxicology.

SUMMARY OF THE INVENTION

The present invention provides a method of evaluating the genotoxic activity of compounds in a bacterial forward mutation assay that is based on resistance to 5-fluorouracil (5-FU). The disclosed assay utilizes a single indicator strain which allows for a higher throughput and significantly reduces the amount of test compound that is required. The validation data presented herein indicates that the 5-FU assay detects a variety of mutagens.

Forward mutation assays, such as the assay disclosed and claimed herein, detect gene mutations which alter the genome of a tester strain from a wild-type condition to a mutant condition (Skopek, T. R., et al., (1983) *Mutation Res.* 108:45-56). The use of a forward mutation assay design as the basis of a high throughput test system is desirable for several reasons, including its sensitivity to multiple types of mutational events (e.g., base substitutions, frameshift, small insertions/deletions), its use of a single tester strain, resulting in a small requirement of test compound for screening, and the potential for a high throughput screening due to a multiwell format.

The disclosed assay specifically identifies genotoxic agents that introduce mutations which have the effect of conferring drug resistance to 5-FU. The data provided herein establish that the sequence changes in the uracil phosphoribosyl transferase (upp) gene is the major mechanism involved in 5-FU resistance and the spontaneous mutational spectra of the *Salmonella* upp locus suggests that the upp gene provides a mutational target which is capable of detecting a diverse spectrum of mutagenic events, thereby making it is an ideal locus to target in a forward mutation assay.

The present invention provides a novel forward mutation assay based on resistance to the pyrimidine analog 5-fluorouracil (5-FU) which utilizes a strain of *Salmonella typhimurium* derived from the Ames strain TA100. Accordingly, the invention provides an alternative format to the standard Ames *Salmonella* his+ plate incorporation assay which utilizes a single tester strain, and which has minimal compound requirements. For example, the genotoxicity of a test compound can be determined using (approximately) 30 mgs (e.g., approximately 25, 30, 35, 40, 45 or 50 mgs) and can be performed in liquid suspension. Both of these considerations make the assay amenable to a high throughput format. The disclosed assay is demonstrated herein to be sensitive to a variety of mutagens, including highly toxic genotoxic agents that are difficult to detect in the standard Ames his+ plate assay.

In another aspect, the invention also describes a *Salmonella typhimurium* tester strain, exemplified herein as the FU100 [his+, rfa, ΔuvrB, pkM101, 5-fluorouridine resistant (FUR$^R$] strain for use in the disclosed assay system. The FU100 test strain is derived from the standard Ames strain TA100 and benefits from the genetic characteristics present in the TA100 strain, including: lack of DNA excision repair (uvrB); a deep rough mutation to facilitate transport of large compounds into the cell (rfa); and utilization of an error prone polymerase that is carried on the pKM101 plasmid and which is capable of bypassing lesions (Maron, D. M., et al., (1983) *Mutation Res.* 113:173-215). Using the information provided herein a skilled artisan can easily produce a suitable tester strain for use in the forward mutation assay described herein.

Briefly, in order to practice the disclosed mutation assay one-ml aliquots of exponentially growing bacteria are exposed to the test agent for two hours in the presence and absence of a metabolic activation system, such as a mammalian (i.e., rat, hamster or human) liver homogenate (S9-fraction or liver microsomal enzymes). The aliquots are then diluted, allowed to grow for 3 hours, and assessed for treatment-related toxicity/inhibition by optical density. The cultures are subsequently diluted a second time and grown overnight to permit full recovery from toxicity and to allow expression of the FU$^R$ phenotype. Samples of the cultures are then plated in 384-well microtiter dishes in the presence of 2 μg/ml 5-FU and the pH-sensitive indicator bromcresol purple. Three days later positive wells containing FU$^R$ colonies are detected by their yellow color and enumerated. Treated cultures are then compared to control plates to determine genotoxic activity.

In summary, the invention provides a method which targets the *Salmonella* upp locus as a novel mutational target for use in a genotoxic forward mutation assay that is demonstrated herein to be capable of identifying a variety of mutational events, utilizes a small quantity of compound, and is amenable to the high throughput evaluation of the genotoxicity of a diverse range of compounds. The sensitivity of the assay benefits from the above-described genetic characteristics which have the effect of enhancing the responsiveness of the tester strain to genotoxic agents.

The present invention is described in the following Experimental Details Section, which is set forth to aid in an understanding of the invention, and should not be construed to limit in any way the invention as defined in the claims which follow thereafter. Other features and advantages of the invention will be apparent to those of skill in the art upon further study of the specification and claims.

BRIEF DESCRIPTION OF THE DRAWINGS

FIG. 1 sets forth SEQ ID NO.:1 comprising 2520 base pairs which encodes a *Salmonella typhimurium* derived uracil transport protein (uraA protein) and a Uracil Phosphoribosyl Transferase protein (upp/UPRT). The coding region of the upp gene is defined by nucleotides 215-841, and the coding region for uraA is defined by nucleotides 929-2218.

FIG. 2 presents the amino acid sequence of SEQ ID NO.:2 which comprises Uracil Phosphoribosyl Transferase Protein derived from *Salmonella typhimurium*, which is encoded by a coding region of SEQ ID NO.:1.

FIG. 3 presents the amino acid sequence of SEQ ID NO.:3 which comprises the Uracil Transport Protein derived from *Salmonella typhimurium*, which is also encoded by a second coding region of SEQ ID NO.:1.

FIGS. 5A and 5B are line graphs illustrating the effect of overnight grow back on the plating efficiency of FU$^R$ clones detected in forward mutation assays performed to evaluate the toxicity of Methylmethane sulfonate (FIG. 2A) and 2-Nitrofluorene (FIG. 5B). Tester strains were plated in 2 Tg/ml 5-FU following a 3 hr post-treatment incubation (■) and after an additional overnight grow back at 30° C. (▲). Culture survival measured as OD$_{600}$ at 3 hr is also presented to reflect general toxicity (♦).

DETAILED DESCRIPTION OF THE INVENTION

Figure 4:
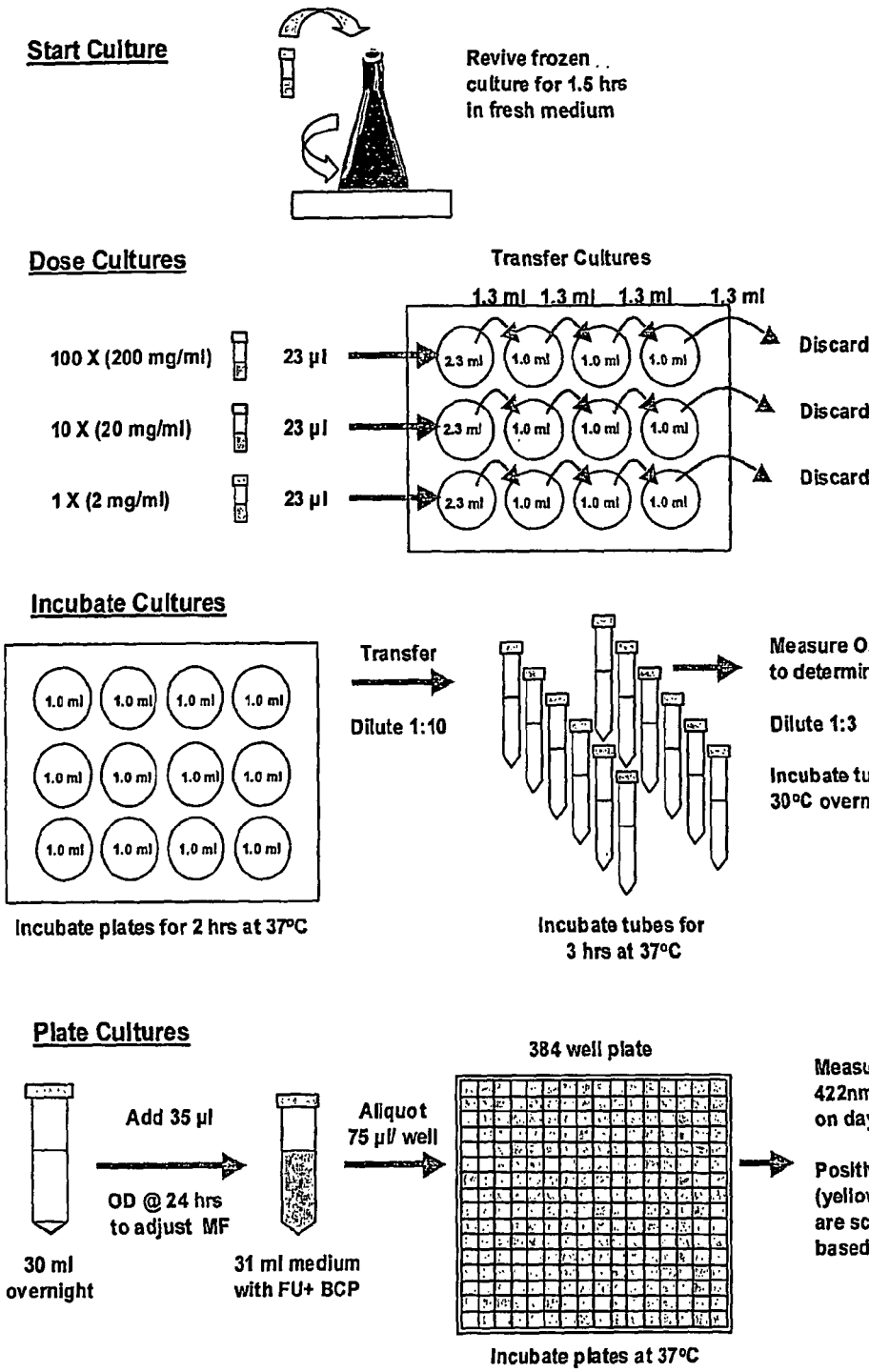
FIG. 4 provides a schematic representation of the experimental protocol for the forward mutation assay based on FU resistance.

It must be noted that as used herein and in the appended claims, the singular forms "a", "an", and "the" include plural reference unless the context clearly dictates otherwise. Thus, for example, reference to "a microbial indicator cell" includes a plurality of such indicator cells, and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, preferred methods, devices, and materials are now described.

In the description that follows, a number of terms used in the fields of genetic toxicology and recombinant DNA technology are extensively utilized. In order to provide a clearer and consistent understanding of the specification and claims, including the scope to be given such terms, the following definitions are provided.

A "gene" refers to a nucleic acid molecule whose nucleotide sequence codes for a polypeptide molecule. Genes may be uninterrupted sequences of nucleotides or they may include such intervening segments as introns, promoter regions, splicing sites and repetitive sequences. A gene can be either RNA (ribonucleic acid) or DNA (deoxyribonucleic acid). A preferred gene is one that encodes the invention peptide.

The term "nucleic acid" or "nucleic acid molecule" is intended for ribonucleic acid (RNA) or deoxyribonucleic acid (DNA), probes, oligonucleotides, fragment or portions thereof, and primers. DNA can be either complementary DNA (cDNA) or genomic DNA, e.g. a gene encoding the invention peptide.

Unless otherwise indicated, a nucleotide defines a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Each "nucleotide sequence" set forth herein is presented as a sequence of deoxyribonucleotides (abbreviated A, G, C and T). However, by "nucleotide sequence" of a nucleic acid molecule is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO.: 1 set forth using deoxyribonucleotide abbreviations is intended to indicate an RNA molecule having a sequence in which each deoxyribonucleotide A, G or C of SEQ ID NO.: 1 has been replaced by the corresponding ribonucleotide A, G or C, and each deoxyribonucleotide T has been replaced by a ribonucleotide U.

As used herein the term "genotoxicity tests" broadly encompasses numerous in vitro or in vivo tests designed to detect compounds (drugs or their reactive metabolites) for their ability to directly or indirectly induce genetic damage by various mechanisms of action.

The "Ames test" is a reverse mutation or reversion assay which measures his⁻ to his+ reversion induced by mutagens that cause base changes or frameshift mutations in the genome of the microorganism *Salmonella typhimurium*. More specifically, the Ames test detects mutations in a gene of a histidine-requiring strain of bacteria which have the affect of producing a histidine-independent strain.

An "auxotroph" is a mutant bacterial strain that is incapable of growth on minimal medium. Accordingly, auxotrophs routinely require the presence of a particular nutrient which its corresponding wild-type strain (prototroph) does not require. For example, the standard *S. typhimurium* tester strains used in the Ames test are auxotrophic for the amino acid histidine and can only be grown in culture media that is supplemented with histidine.

An "insertion" or "addition", as used herein, refers to a change in an amino acid or nucleotide sequence resulting in the addition or insertion of one or more amino acid or nucleotide residues, respectively, as compared to the corresponding naturally occurring molecule.

An "deletion" or "subtraction", as used herein, refers to a change in an amino acid or nucleotide sequence resulting in the deletion or subtraction of one or more amino acid or nucleotide residues, respectively, as compared to the corresponding naturally occurring molecule.

A "substitution", as used herein, refers to the replacement of one or more amino acids or nucleotides by different amino acids or nucleotides, respectively.

A "mutation" is a heritable change in a DNA sequence relative to a reference "wild-type" DNA sequence. Mutations can occur as a result of a single base change, multiple base changes, or the addition or deletion of more than one nucleotide to a DNA sequence.

The term "genotoxicity" is used to broadly refer to any deleterious change in the genetic material of a cell, regardless of the mechanism by which the change is induced.

As used herein the term mutagenicity and genotoxic activity are used to refer to the ability of an agent (e.g., a chemical compound or a drug candidate) to cause a permanent change in the structure of the genetic material of a cell which causes a heritable change in the effected cell. Contemplated changes include alterations in the sequences of the bases in the nucleic acid (gene mutation), structural changes to chromosomes (clastogenicity) and/or changes to the number of chromosomes present.

A "mutagen" or a "genotoxic agent" is an agent that creates or causes mutations. It is well-established that chemical mutagens vary in their modes of action. However, in general terms, a chemical mutagen changes a nucleic acid or nucleoside relative to the nucleotide sequence of a reference or "wild-type" genome. Generally speaking a mutagen or genotoxic agent increases the frequency of reversion or forward mutation.

A "gene mutation" refers to a mutation that occurs entirely within one gene, or its upstream regulatory sequences and can comprise either a point mutation or other disruption of normal chromosomal structure that occurs entirely within one gene.

A "reversion assay" is an assay of genotoxic activity which detects a reverse mutation which confers normal function to a mutant gene thereby causing a gain of function. Typically, the genotoxic activity of compounds are evaluated using a bacterial reverse mutation assay that utilizes an amino acid-requiring (i.e., auxotrophic) tester strains of *Salmonella typhimurium* (*S. typhimurium*) or *Escherichia coli* (*E. coli*) to evaluate the genotoxic activity of a compound. Generally speaking, reversion assays are capable of detecting point mutations, such as a substitution, an addition or a deletion of one or more DNA bases, which are introduced into the genome of an affected tester strain.

A "forward mutation assay" is an assay of genotoxic activity which detects "forward" mutations that alter a functional gene in a way that causes a loss, rather than a gain, of function.

A "wild-type" bacterial strain is capable of a full range of metabolic activities. For example, wild-type strains of *Salmonella* can synthesize all 20 amino acids from a single carbon source.

A "mutant" bacterial strain is not capable of all of the activities of the wild-type strain from which it is derived. For example, a mutant bacterial strain that is defective in its ability to synthesize the amino acid histidine (his⁻ strain) requires the presence of exogenous histidine in order to grow.

A "point mutation" is a change in one, or a small number of base pairs, in a DNA sequence. Point mutations may result from base pair substitutions or from small insertions or deletions.

A "transition" is a point mutation in which a purine is replaced with a purine or a pyrimidine is replaced with a pyrimidine.

A "transversion" is a point mutation in which a purine is replaced with a pyrimidine or a pyrimidine with a purine. Generally speaking, transitions are more common than tranversions because the former are not detected by the proof-reading enzymes.

Alternatively, point mutation can also cause a nonsense mutation resulting from the insertion of a stop codon (amber, ochre, opal), Base pair mutations that generate a translation stop codon causes premature termination of translation of the coded protein.

A "frameshift mutation" results from the insertion or deletion of one or more nucleotides within a gene. The "reading frame" of a gene refers to the order of the bases with respect to the starting point for translation of the mRNA. Deletion of a single base pair results in moving ahead one base in all of the codons, and is often referred to as a positive frameshift. Addition of one base pair (or loss of two base pairs) shifts the reading frame behind by one base, and is often referred to as a negative frameshift.

As used herein the term "DNA Repair Mechanism" refers to any one of the potential repair mechanisms which exist in both prokaryotes and eukaryotes. For example: postreplication; mismatch repair; nucleotide excision-repair and photo-reactivation or light-dependent repair (not found in mammals).

A "base pair substitution mutagen" is an agent that causes a base (i.e., nucleotide) change in DNA. In the context of a reversion test this change may occur at the site of the original mutation, or at a second site in the bacterial genome.

A "frameshift mutagen" is an agent that causes the addition or deletion of one or more base pairs in the DNA, thus changing the reading frame in the RNA.

As used herein, "uracil phosphoribosyltransferase gene" or "upp" refers to a uracil phosphoribosyltransferase gene derived from *Salmonella typhimurium* that is encoded by a nucleic acid molecule of SEQ ID NO.: 1 (see FIG. 1). It also includes nucleic acid molecule that hybridizes under high stringency conditions to the nucleotide sequences disclosed herein. Such nucleic acid molecule can be characterized in a number of ways, for example, the DNA may encode the amino acid sequence (upp/UPRT) set forth in SEQ ID NO.: 2, or the DNA may include the nucleotide sequence as set forth in FIG. 1. The arbitrary numbers for the entire nucleotide sequence set forth in SEQ ID NO.:1 are nucleotides 1-2520, the coding sequence for the uracil transferase protein of SEQ ID NO.:2 being defined by nucleotides 215 to 841 (SEQ ID NO.: 4), for a total of 627 base pairs that encode for a 208 amino acid protein.

As used herein, "uracil transport gene" or "uraA" refers to a uracil transport protein (uraA protein) encoding gene derived from *Salmonella typhimurium* that is encoded by a second coding region contained within the nucleic acid sequence set forth in SEQ ID NO.: 1 or one that hybridizes under high stringency conditions to coding sequence disclosed herein. Such nucleic acid molecule can be characterized in a number of ways, for example, the DNA may encode the amino acid sequence set forth in SEQ ID NO.: 3 (see FIG. 3), or the DNA may include the nucleotide sequence as set forth in SEQ ID NO.: 1. The coding sequence for the uraA is from nucleotides 929-2218 (SEQ ID NO: 5) as contained in FIG. 1 which encodes a protein comprising the amino acid sequence set forth in SEQ ID NO.: 3 (429 amino acids encoded by 1290 base pairs) (see FIG. 2).

As stated above, the Ames *Salmonella* his+ plate incorporation assay evaluates genotoxic activity (mutagenicity) of chemical compounds on a set of genetically modified bacterial tester strains that are auxotrophic for the amino acid histidine. In practice, the Ames Assay simultaneously evaluates the genotoxic activity of a potential mutagen on several different target genes. The standard Ames Assay utilizes several different tester strains, each with a distinct mutation (e.g., transition, frameshift etc.) in one of the genes comprising the histidine (his) biosynthetic operon. The his operon encodes enzymes required for the biosynthesis of the amino acid histidine. For example, strain TA98 contains the hisD3052 allele which is reverted by a frameshift mutation, while strain TA1535 contains the hisG46 allele which is reverted by transition and transversion mutations. More specifically, the Ames Assay evaluates the ability of a chemical agent to increase the rate of reversion of auxotrophic strains of *Salmonella* to prototrophy.

Wild-type strains of *S. typhimurium* synthesize the amino acid histidine, which is generally not present in synthetic minimal culture media. The tester strains used in the Ames Assay are auxotrophic for histidine and can only survive and grow on medium that is supplemented with histidine. The detection of revertant (i.e., mutant) bacteria in test samples that are capable of growth in the absence of histidine indicates that the compound under evaluation has genotoxic (i.e. mutagenic) activity. Thus, the underlying principle of a bacterial reverse mutation assay, such as the Ames Assay, is that it identifies genotoxic agents (mutagens) which introduce changes (e.g., mutations) that reverse mutations present in a genetically engineered tester strain and restores the functional capability of the tester strain to synthesize a particular amino acid.

After exposure to an agent with genotoxic activity, some of the Ames tester strains may regain the ability to synthesize histidine and will consequently acquire a phenotype which allows it to grow on histidine-deficient media. By comparing the number of colonies of each strain grown in the presence of an agent that is being evaluated for genotoxic activity relative to the number of spontaneous revertants that occur in the absence of any agent an investigator can determine whether the agent has genotoxic activity and if so, what type of mutation it causes. A similar assay can also be conducted using *E. coli* tester strains that are auxotrophic for the amino acid tryptophan.

In order to increase the probability of detecting genotoxic activity the standard Ames mutation assay uses a combination of several, typically four or more, tester strains of *Salmonella*. The use of multiple tester strains increases the probability that the genotoxic activity of a mutagenic or genotoxic agent or compound will be detected. The most frequently used *Salmonella* tester strains are TA97, TA98, TA100, TA102, TA104, TA1535, TA1537, and TA1538. Although all of the tester strains are auxotrophic for histidine, each of the strains is genetically distinct. The mutations which render the tester strains auxotrophic include a variety of in-frame mutations (such as base-pair substitutions) and frameshift mutations (such as base-pair deletions or insertions). More specifically, each strain comprises a mutation in a gene that encodes a protein product that is required for the histidine biosynthetic pathway. Each of the mutations has the affect of preventing the tester strain from synthesizing the essential amino acid histidine from the nutrients present in standard bacterial culture medium. Generally speaking, knowledge of the particular mutation carried by a revertant tester strain can provide useful information on the types of mutations that is induced by a mutagen.

Many of the Ames tester strains of *S. typhimurium* are characterized by additional features that increase the sensitivity of the strain with respect to its ability to detect genotoxic activity. Useful characteristics include, but are not limited to, responsive DNA sequences at the reversion sites; increased cell permeability to large molecules; elimination of DNA repair system and enhancement of error-prone DNA repair processes. For example, the lipopolysaccharide cell wall of some tester strains, including TA97, TA98, TA100, TA102 and TA104 has been weakened so that it no longer excludes large molecules This characteristic allows many putative mutagens to enter the cell; thereby making particular classes of mutagens amenable to screening in the Ames assay.

Other tester strains have been engineered to comprise a defective DNA repair system which is mediated by deletion the urvB gene and which prevents the tester strains from correcting damaged DNA bases. In addition, in an attempt to increase strain sensitivity and reliability, the pAQ1 or pKM101 plasmids (extrachromosomal circular DNA) have been added to some of the tester strains. The plasmid pAQ1 carries a tetracycline resistance gene and a copy of His G428 in the context of a multicopy plasmid. The pKM101 plasmid carries an error-prone DNA polymerase and an ampicillin resistance gene. Other plasmids that may contain error-prone DNA polymerases include, but are not limited to, those presented in W. H. Koch, et. al., Mut Res 457 (2000) 1-13.

It is recognized that prokaryotic cells differ from mammalian cells in such factors as uptake, metabolism, chromosome structure and DNA repair processes. Some chemicals (compounds) are not mutagenic (genotoxic) in their native forms, but are converted into mutagenic substances (reactive products) by metabolism in the liver while other compounds are detoxified as a result of liver metabolism. Therefore, because bacteria do not have the same metabolic processes as mammals, genotoxic assay protocols which utilized non-mammalian indicator cells (e.g. microbial cells) often involve pretreatment of the test compounds with a metabolic activation system such as a mammalian liver homogenate (usually a S9 fraction or extracts of rat or hamster liver enzymes) to promote metabolic conversion (e.g. cytochrome P450 mediated conversion) of the test compound.

Some mutagenic compounds are active with and without metabolism, while others are active only under one condition or the other. Thus, the genotoxic activity of potential mutagens are typically evaluated with and without exposure to a metabolic activation system. Any suitable metabolic activation system can be used to activate the test compound prior to evaluating its genotoxic activity in the forward mutation assay described herein. Preferred metabolic activation systems, which are widely accepted under the guidelines formulated by the regulatory agencies of various countries include mammalian S9 preparations. Procedures for the preparation and use of suitable activation systems are well known in the art [see, for example, Current Protocol in Toxicology, Unit 3, 1, *The Salmonella (Ames) Test for Mutagenicity*, Support Protocol 5: Preparation of Metabolic Activation System (S9); Ames, B. N. et al.]. One of skill in the art will appreciate that a combination of the enzymes that are typically present in a S9 preparation and which are known to play a role in metabolic activation can alternatively be used to activate/pretreat test compounds.

It is widely recognized that incorporation of an in vitro metabolic activation system cannot entirely mimic the effects of mammalian metabolism; thus it is widely accepted that an in vitro screening assays utilizing prokaryotic indicator cells cannot provide direct information on the in vivo genotoxicity of pharmaceutical compounds and/or their reactive metabolites to humans. This experimental limitation partially explains why the standard four-test battery includes tests which utilize mammalian cells and includes an in vivo evaluation of genotoxicity.

The present invention provides a high throughput bacterial forward mutation assay which utilizes a single tester strain to screen for a variety of mutational events including base pair substitutions, frameshifts, and the insertion or deletion of more than one nucleotide into the genome of the tester strain. Those of skill in the art will appreciate from the present description that any suitable assay format can be used to practice the genotoxicity assay described herein. Due to the fact that a forward mutation assay can theoretically detect any change that inactivates the target gene (forward mutation marker or target gene), it is reasonable to assume that only one bacterial strain could be used to detect all six types of base substitution mutations, a variety of frameshift types, and large deletions or insertions within the target gene (Skopek, T. R., et al., (1983) *Mutation Res.* 108:45-56). The data presented herein confirms the above-referenced theoretical expectation, because when considered together it establishes that resistance to 5-FU can result from a variety of mutations in different sequence contexts in the uracil phosphoribosyl transferase (upp) gene. The ability to utilize a single tester strain reduces the amount of compound that is required to assess the mutagenic potential of a test compound, an advantage which makes it feasible to evaluate the genotoxicity of drug candidates at a relatively earlier stage of the drug development process, at a point in time when agents may only be available in small quantities.

The present invention also identifies the upp gene as a mutational target and describes how to isolate a suitable tester strain for use in the assay of the invention. The disclosed forward mutation assay is exemplified herein by the use of a tester strain, designated herein as FU100. The FU100 strain is derived from Ames tester strain TA100 (rfa, ΔuvrB, pkM101) (Ames, B. N. *Enviorn. Health Perspect.* 6: 115-118 (1973). Strain TA100 comprises a hisG46 target allele and benefits from the genetic characteristics conferred by the lack of DNA excision repair (uvrB); a deep rough mutation to facilitate transport of large compounds into the cell (rfa); and utilization of an error prone polymerase contributed by the pkM101 plasmid that is capable of bypassing lesions. TA100 detects transition and transversion mutations as well as some frameshift mutations. The Ames TA100 strain was modified by first selecting a spontaneous histidine revertant (his+) to allow growth without histidine. Subsequent selection in 5-fluorouridine clone avoids unwanted toxicity resulting from cross-feeding of 5-fluorouridine between wild-type and FU-resistant (5-fluorouridine) cells. The resulting tester strain is designated herein as FU100 (his+, rfa, ΔurvB, pKM101, $FUR^R$). This novel indicator strain is used to exemplify the method of the invention, because it has a suitable frequency of spontaneous reversion and it will result in data that is likely to be regarded as directly comparable to data produced in the widely accepted Ames test since the indicator is derived from the well-known TA100 strain.

Based on the information provided herein, regarding the role of the upp gene in the biochemical pathway which confers 5-FU resistance, and the contribution of pKM101 and other genetic elements to the sensitivity of the indicator strain, it is well within the abilities of a skilled artisan to prepare an equivalent tester strain for use in the assay of the invention. Those skilled in the art will understand that any bacterial tester strain suitable for use in a forward mutation assay which utilizes 5-FU resistance to target the upp gene as a mutational marker that can be used in the present invention. The original TA100 strain was selected to prepare an exemplary indicator strain because it was appreciated that the assay would provide data that could be correlated with historical data collected in the standard Ames assay thereby facilitating the validation of the new protocol.

The inventors were also of the opinion that an alternative assay which utilizes a new tester strain that has been developed from a well-known indicator strain would be more readily accepted by regulatory authorities. However, other bacterial strains, including for example, but not limited to, other strains of *Salmonella* (e.g., TA102) or *E. coli* indicator strains that have been engineered to comprise pKM101, such as but not limited to WP2 or WP2urvA [McCalla, D. R. et al., *Mutation Res.* 31(1): 31-37 (1975] can also be used to prepare an indicator strain that is suitable for use in the methods of the invention.

upp of bacterial origin catalyzes the conversion of uracil and 5-phosphoribosyl α-1-pyrophosphate (PRib-PP) to uridine-5'-monophosphate (UMP) and $PP_i$. See Neuhard et al., *Metabolism of Nucleotides, Nucleosides and Nucleobases in Microorganisms* (Munich-Petersen A., ed.) Academic Press, New York, 95-148. Generally speaking, pyrimidine salvage enzymes enable cells to utilize preformed nucleobases and nucleosides either from the growth medium or from degradation products of cellular nucleic acids. The role of uracil phosphoribosyltransferase in the salvage of endogenously formed uracil and in the utilization of exogenous uracil and cytosine has been demonstrated in several microorganisms including *Escherichia coli*.

Importantly, bacterial uracil phosphoribosyltransferase is functionally equivalent to orotate phosphoribosyltransferase or uridine-5'-monophosphate synthase of mammalian cells. These enzymes mediate the conversion of 5-fluorouracil (5-FU) (a fluorinated analog of uracil) to 5-fluorouridine 5' monophosphate (5-FUMP). 5-fluorouridine 5' monophosphate is subsequently converted to 5-FdUDP and FdUTP via the mammalian de novo pyrimidine pathway. Each 5-FdUTP is an irreversible inhibitor of thymidylate synthase (Thy-A) and results in dTTP starvation. It is widely accepted that this conversion is one of the requisite pathways to achieve cytotoxic effects of 5-fluorouracil and that bacterially uracil phosphoribosyltransferase of bacterial origin is able to convert 5-fluorouracil to the same active metabolite as does mammalian orotate phosphoribosyltransferase.

Based on published information from studies designed to elucidate the molecular basis of 5-FU-resistance in *E. coli*, it was theorized that two genes, the uracil phosphoribosyl transferase gene (upp) or the uracil transport protein (uraA) were likely to be involved in conferring 5-FU-resistance (O'Donovan, G., et al., (1970) *Bacteriol. Rev.* 34:278-343); (Andersen, P. S., et al., (1992) *Eur. J. Biochem.* 204:51-56).

The upp gene from *E. coli* had been previously isolated by Anderson et al., *Eur J. Biochem,* 204: 51-56 (1992). (Andersen et al., 1992). The work described herein involved the cloning of the *Salmonella typhimurium* upp and uraA homologues and correlating 5-FU-resistance with the upp locus.

The upp and uraA genes were cloned and sequenced using PCR primers designed to be complementary to their *E. coli* homologs. More specifically, a 2500-nucleotide sequence containing both genes was determined, which contains a single transcriptional promoter located between 50 and 80 bases upstream from the ATG start codon for the upp gene. The uraA start codon was identified 86 bases downstream of the upp start codon. There does not appear to be any transcriptional promoter sequences between the two genes, indicating that both genes are translated from a polycistronic message, similar to that found in *E. coli*.

Mutants of *Escherichia coli* which possess an intact uracil transport system, but lack a functional upp enzyme, are unable to utilized uracil as a pyrimidine source and consequently excrete uracil into the culture medium. See Malloy A., et al. *FEBS Letts.*, 5: 211-213 (1969). Based on these observations and the functional equivalence between bacterial uracil phosphoribosyltransferase and orotate phosphoribosyltransferase or uridine-5'-monophosphate synthase of mammalian cells, it was theorized that mutations in the upp gene which have the effect of disrupting the function of the uracil phosphoribosyltransferase enzyme could confer resistance to 5-fluorouracil (a fluorinated analog of uracil).

Consistent with this prediction it had been observed that the bacterial mutants which lack a functional upp enzyme are resistant to 20 μM 5-fluorouracil. The data provided herein establish that 5-FU-resistance provides a phenotype that can be used to select mutants comprising an altered upp gene and that as a target gene, bacterial upp is responsive to a variety of induced mutations including base pair substitutions, frameshifts, and the insertion or deletion of one or more nucleic acids. Considered together, these findings establish that the upp gene provides a sensitive target for the detection of a variety of induced mutations in *Salmonella*.

A study was then conducted to determine the optimal concentration of the selective agent 5-FU. The growth rate was determined for cultures in MinE containing up to 8 μg/ml 5-FU. Cultures containing less than or equal to 0.5 μg/ml continued to grow, albeit at longer doubling times as the concentration increased, while those with greater than or equal to 1 μg/ml 5-FU significantly inhibited culture growth (data not shown). The concentration of 2 μg/ml 5-FU was chosen for selection of 5-FU-resistant clones in subsequent mutation assays. Based on the teachings provided herein, a skilled artisan can easily determine the optimal concentration of 5-FU to use in an alternative version of the forward mutation assay disclosed herein. A suitable selective concentration for use in an equivalent assay is likely to be greater than one 1 μg/ml 5-FU and less than 10 μg/ml 5-FU. For example, depending upon the genetic elements present in the indicator strain the optimal selective concentration of 5-FU could be 1 μg/ml, 2 μg/ml, 3 μg/ml, 4 μg/ml, 5 μg/ml, 6 μg/ml, 7 μg/ml, 8 μg/ml, 9 μg/ml, or 10 μg/ml.

The FU assay design (as disclosed and claimed herein) is performed as described in FIG. 4. All of the attributes of the assay are presented therein. Another advantage of the assay design disclosed and claimed herein is that it allows the assessment of treatments producing significant toxicity in the population. The induction of mutations and the induction of toxicity can be (and usually are) two independent events. Evidence for this comes from the fact that there are potent mutagens that produce large increases in mutation frequency while inducing little toxicity, compounds that are non-mutagenic but very toxic, and compounds that lie between these two extremes. The overnight grow-back period included in the protocol permits the detection of increases in mutation frequency (mutants per surviving cell) even when they are accompanied by severe toxicity.

Generally speaking, signal-to-noise, or the magnitude of induced mutation frequency relative to spontaneous frequency determines the ultimate sensitivity that can be achieved by a particular assay design. In a reversion assay, the "noise" or background is very low because only those genetic events resulting in reversion of the primary mutation will be scored. If the compound under study reacts efficiently at the target sequence for reversion, then a very favorable signal to noise ratio is achieved. However, if the agent fails to react at the sequence or reacts inefficiently, then a poor signal-to-noise ratio is realized. This consideration is the reason why multiple tester strains are typically used in the Ames reversion assay protocol. However, it is acknowledged that even with the use of several strains, there is the possibility the "ideal" target sequence required to detect the genotoxic activity of a particular mutagen may not be represented.

In a forward mutation assay, a large number of different spontaneous events at a number of different bases in the target gene could contribute to the overall background mutation rates observed in the system. Given the size of a typical gene and the diversity of sequence contexts within, it is likely that a particular sequence context favored by a given chemical mutagen will be represented at multiple sites in the target gene. This results in a favorable signal-to-noise ratio in the test samples following treatment with the agents that are being evaluated. If, however, the sequence context preferred by a chemical is not present or present in limited numbers in the gene, a less favorable signal-to-noise ratio would be realized. Therefore, one might expect that with some compounds reversion may be more sensitive than a forward mutation assay, while for other compounds, a forward assay may be more sensitive.

Examples of both of the above-described situations can be observed in the data provided herein for some of the test compounds included in the panel of the validation compounds evaluated in the forward mutation assay disclosed herein. For example, in the standard Ames assay, both TA1535 and TA100 are extremely sensitive to sodium azide toxicity at microgram concentrations in both the standard plate incorporation format and when bacteria are treated in liquid suspension (data not shown). However, a concentration greater than 90 µg/ml sodium azide is required to produce a positive response in the 5-FU Assay. A second example of the favorable signal-to-noise ratio that characterizes the 5-FU assay disclosed herein can be seen in the data resulting from the evaluation of the genotoxicity of cyclophosphamide. Using a standard Ames assay protocol (plate incorporation or liquid suspension) and either the TA100 or T1535 indicator strains, Cyclophosphamide is positive; however only a weak positive is observed at the highest doses tested in the 5-FU Assay. Conversely, the 5-FU Assay responds positively to 0.4 µg/ml benzo[a]pyrene, while extremely high, precipitating doses (>20 µg/ml) are required to elicit a meager response in TA100. Three other examples of compounds that were easy to detect in the 5-FU Assay but only produce a weak or equivocal response in the Ames assays are benzyl chloride, 1,2-epoxybutane, and hydrogen peroxide.

It was recognized that reducing the background mutation frequency by eliminating preexisting $FU^R$ mutants could increase the sensitivity of the assay. Since the only mechanism leading to 5-FU resistance in Salmonella involves loss of uracil phosphoribosyltransferase, a uracil salvage enzyme and product of the upp gene, it was theorized that blockage of the de novo pyrimidine synthesis and supplementation with uracil should permit growth of wild-type cells and selection against $FU^R$ upp mutants.

It was determined that 50 µg/ml 5-fluorooroticacid, an inhibitor of de novo pyrimidine synthesis, inhibited growth of wild-type cells, and that this inhibition could be reversed by the addition of 20 µg/ml uracil. It was also determined that upp mutants cannot grow in the presence of 5-fluorooroticacid and uracil, presumably due to their inability to utilize exogenous uracil. As expected, the $FU^R$ mutant frequency of cultures grown in the presence of 5-fluorooroticacid and uracil was significantly reduced relative to control cultures (approximately 20-fold). Frozen stocks of FU100 were prepared using cultures grown under these conditions (described in Materials and Methods) in order to produce "cleansed" working stocks with reduced background.

Use of these "cleansed" frozen vials under standard FU Assay conditions resulted in lower control mutant frequencies. Controls values were reduced from an average of 0.25 adjusted mutants per well without S9 and 0.20 with S9 (average of 160 and 120 wells per 384-well plate, respectively) to an average of 0.11 adjusted mutants per well without S9 and 0.11 with S9 (average of 90 and 80 wells per 384-well plate, respectively) when "cleansed" frozen cultures were used (Table 8). It should be noted that the reduction in background mutant frequency seen under actual assay conditions was not as profound as that observed in cultures grown in the presence of 5-fluorooroticacid and uracil, suggesting that most of the mutants scored in the 5-FU Assay are generated during the conduct of the assay.

The results obtained with the validation compounds are summarized in Table 9 and indicate a 100% correlation with the results obtained using the traditional Ames assay. Considered together, these results support the feasibility of using the 5-FU Assay as an alternative screen to the Ames assay. An advantageous feature of the assay described and claimed herein includes the fact that the system requires the use of only a single tester strain and the protocol can be performed in liquid suspension using standard microtiter plates which offers the ability to automate part or all of the assay, thereby increasing its potential throughput. In addition, the compound-sparing nature of the 5-FU assay (which typically requires less than 50 milligrams of compound per assay), its ability to detect the gentoxic activity of a variety of chemical mutagens, and its ability to detect very toxic mutagens makes it an attractive screening assay when compound availability is limiting.

Based on the present description, one skilled in the art will readily appreciate that the methods of the present invention can be readily carried out and confer substantial cost- and time-savings when compared with the standard Ames test. Cost savings will result from the decreased quantity of test compound that is required, and time savings will result form the advantages conferred by using a single indicator strain and not having to manually count revertant colonies against a lawn of non-revertant colonies.

In addition, the disclosed assay are clearly amenable to being scaled up to a high throughput format and because the indicator strain used herein (FU100) was derived from the Ames TA100 standard it will produce data that will be directly comparable to data that has been historically generated in the standard Ames assay. Given the highly proscribed nature of the pharmaceutical industry it is reasonable to assume that an alternative genotoxic assay that is capable of generating data that can be directly compared to obtained from a Standard Ames assay is more likely to be accepted.

All publications mentioned herein are incorporated herein by reference for the purpose of describing and disclosing methodologies, bacterial tester strains etc. which are reported in the publications that might be used in connection with the invention. Nothing herein is to be construed as an admission that the invention is not entitled to antedate such disclosure by virtue of prior invention. Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

Materials and Methods

Chemicals and Reagents d-Biotin, bromcresol purple sodium salt, citric acid monohydrate ($C_6H_8O_7.H_2O$), dimethyl sulfoxide (DMSO), D-(+)-glucose, glucose-6-phosphate, magnesium chloride hexahydrate ($MgCl_2.6H_2O$), magnesium sulfate heptahydrate ($MgSO_4.7H_2O$), potassium chloride (KCl), potassium phosphate anhydrous ($K_2HPO_4$), sodium ammonium phosphate tetrahydrate ($NaNH_4PO_4.4H_2O$), sodium phosphate anhydrous ($Na_2HPO_4$), sucrose, uracil, 2-aminoanthracene (2-AA), 5-fluoroorotic acid, 5-fluorouracil (5-FU), and 5-fluorouridine were purchased from Sigma Aldrich (St. Louis, Mo.). Casamino acids were obtained from Fisher Scientific (Pittsburgh, Pa.). Bacto-Agar was from Difco (Detroit, Mich.), nicotinamide-adenine dinucleotide phosphate (NADP) was from Boehringer Mannheim (Indianapolis, Ind.), and deionized water was from Life Technologies (Carlsbad, Calif.). Male rat liver S9 induced with phenobarbital and β-naphthoflavone was purchased from Molecular Toxicology (Moltox, Boone, N.C.). The test compounds assayed in this study are presented in Table 3, along with their CAS number, supplier, solvent and dose range tested.

Bacterial Strains

The *Salmonella typhimurium* strains TA100 (hisG46, rfa, −urvB, pkM101) and TA1535 (hisG46,−urvB) were kindly provided by Dr. B. N. Ames, Biochemistry Department, University of California, Berkeley, Calif. The TA100 and TA1535 strains were further modified by first selection of a spontaneous histidine revertant (his+) and subsequent selection of a fluorouridine-resistant clones FU100 (his+, rfa, −uvrB, pKM101, 5-fluorouride resistant ($FUR^R$) and FU1535 (his+, rfa, −uvrB, $FUR^R$). Both of the indicator strains can be maintained in Minimal E Medium supplemented with biotin, glucose, and casamino acids.

EXAMPLES

Example 1

Determination of DNA Coding Sequence for Uracil Phosphoribosyl Transferase (upp) and Uracil Transport Protein (uraA) from *S. typhimurium*

The upp gene from *Escherichia coli*, which encodes the enzyme uracil phosphoribosyltransferase, has been previously isolated by Anderson et al., *Eur J. Biochem*, 204: 51-56 (1992). Mutants of *Escherichia coli* lacking the enzyme uracil phosphoribosyltransferase, but with an intact uracil transport system, fail to grow on uracil as a pyrimidine source and they excrete uracil into the culture medium. See Malloy A., et al. *FEBS Letts.*, 5: 211-213 (1969). Furthermore, they are resistant to 20 μM 5-fluorouracil, this being a phenotype which has been used in the selection of upp mutants.

Genomic DNA from *Salmonella typhimurium* TA100 and TA1535 was obtained using Qiagen DNeasy Tissue Kit (catalog #69504) as described by the manufacturer. Initial attempts to isolate the *Salmonella* upp gene involved designing PCR primers flanking the known *Escherichia coli* UPRT gene sequence (GenBank accession X57104). These primers were homologous to the *Escherichia coli* sequences (forward: 5' TTT GTG GCT GCC CCT CAA AGG 3' SEQ ID NO.: 6; reverse: 5' AAA AGC CGA CTC TTA AAG TCG GCT T 3'SEQ ID NO.: 7), and proved unsuccessful in amplifying the *Salmonella* upp gene from the purified genomic DNA in several attempts.

The *Escherichia coli* upp gene was then entered into a nucleotide BLAST search engine, which displayed 88% homology to a small portion of a *Salmonella* GenBank submission for the purN and purI gene sequences (accession U68765.1). Approximately 50% of the *Escherichia coli* upp was present at the end of this *Salmonella* purN and purI sequence. By aligning the front half of the *Salmonella* upp sequence with the back half of the *Escherichia coli* upp sequence, a hypothetical upp hybrid was constructed. PCR primers were then designed with a forward primer homologous to the *Salmonella* sequence (Forward-1: 5' TTT GTG GTT GCC AGT CAT CTG AGG 3'(SEQ ID NO.: 8); Forward-2 (Sal upp Forward-1): 5' ATC CAG GTC AAG CAT ACA TTG TGT TG 3'(SEQ ID NO.: 9); Forward-3: 5' AGG ATA TCC AGC ACT TGG TTT ACG AC 3') and several reverse primers homologous to the *Escherichia coli* sequences (Reverse-1 (EC upp Reverse-1): 5' CTG GAT CGC GCA GCA GAT CTT TTT T 3'(SEQ ID NO.: 10); Reverse-2: 5' ATA AGC CGG AAT TTT CCC TTT 3'(SEQ ID No.: 11); Reverse-3: 5' CCC CGC TTT CTT CAC GAT AAA AGA AA 3'(SEQ ID No.: 12)). These *Escherichia coli* primers were designed to anneal within (or prime) homopolymeric runs in *Salmonella*. Amplification from *Salmonella* TA100 and TA1535 genomic DNA yielded the PCR products of the predicted size, which were then purified and sequenced to reveal the *Salmonella* upp nucleotide sequence. Three independent cultures of TA100 were obtained from different sources, and the *Salmonella* upp gene was amplified and sequenced to confirm the DNA sequence. The *Salmonella* upp sequence demonstrated 88% homology to the *Escherichia coli* sequence at the nucleotide level, and 99% homology at the amino acid level.

The *Salmonella* uraA sequence was then determined using a similar approach. First, the *Escherichia coli* uraA sequence was obtained from GenBank (accession AE000336 U00096). Surprisingly, it was noted that the *Escherichia coli* upp resides 86 nucleotides upstream from the uraA start codon. In the previously determined *Salmonella* upp nucleotide sequence, approximately 800 nucleotides downstream from the upp stop codon were determined, accounting for approximately half of the *Salmonella* uraA gene. *Salmonella* forward PCR primers were designed with homology to the determined *Salmonella* sequences (Sal uraA Forward-1: 5' AAA CCA CTC ATA ACA AAC ACA CTT AG 3'(SEQ ID NO.: 13); Sal uraA Forward-2: 5' CGG TGT TCG GCT CCG TAC TGT 3'(SEQ ID NO.: 14)), and *Escherichia coli* reserve PCR primers were then designed to prime homopolymeric runs (EC uraA Reverse-1: 5' CCT CAA CCA GGA TTT CAC AAA 3'(SEQ ID NO.: 15); EC uraA Reverse-2: 5' GCC AGT AAA GAG GAG TTA TCC CC 3'(SEQ ID NO.: 16); EC uraA Reverse-3: 5' CGG AAC AAA CCA GGT GCG TTT 3' (SEQ ID NO.: 17)) in hopes of finding some level of homology to *Salmonella* to allow sufficient amplification by PCR. The Salmonella uraA sequence demonstrated 82% homology to the Escherichia coli sequence at the nucleotide level, and 93% homology at the amino acid level.

The Salmonella upp and uraA amplicons were generated using the following PCR conditions: 15 mM Tris-HCL, pH 8.5, 50 mM KCl, 3, 5 mM MgCL2, 300 uM dNTPs, with 100 ng each primer and 2.5 units Taq polymerase (Applied Biosystems). Reactions were performed with an initial denaturation at 94° C. for 2 minutes, followed by 32 cycles of 94° C. for 15 seconds, 50° C. for 30 seconds, 72° C. for 1 minute, ending with a 3 minute extension at 72° C. Amplification was successful, and the PCR products were then purified and the Salmonella uraA nucleotide sequence determined by automated sequencing.

Three independent cultures of TA100 and TA1535 gene were obtained from different frozen stocks, genomic DNA isolated, and the Salmonella upp and uraA gene amplified and sequenced to confirm the DNA coding sequence. The entire 2500-nucleotide sequence (FIG. 1) containing the coding sequences for both the Salmonella upp and uraA was submitted to GenBank (accession AF427145).

Example 2

Fluctuation Analysis: Isolation of Independent 5-Fluorouracil-Resistant Clones and Determination of the upp Mutation Rate Spontaneous independent mutants resistant to 5-FU (Sigma) were obtained by fluctuation analysis of independent bacterial cultures. Saturated cultures ($1 \times 10^9$ cells per ml) of either FU100 or FU1355 were diluted to a concentration of $2 \times 10^3$ cells per ml, and then 5 ml volumes were aliquoted into independent 15 ml conical tubes (total cells concentration of $1 \times 10^4$ per tube; 100 tubes for FU100, 124 tubes for FU1535). Each $10^4$-cell inoculum was grown overnight to confluency, and 10 microliters of each independent culture plated on 100 mm plates containing 2 ug/ml 5-FU. Colonies were allowed to grow on plates overnight, and the number of 5-FU-resistant ($FU^R$) clones per plate counted. Two individual $FU^R$ clones were isolated from each plate and transferred to agar plates containing 5-FU.

Independent mutants are defined as spontaneous mutants arising from different (e.g., independent) $10^4$-cell inoculas. The average number of colonies per plate and the ratio of plates without colonies were used to estimate mutation rate. The average spontaneous upp mutation rates estimated using two different methods were 30.6 and $2.9 \times 10^{-8}$ for the FU100 and FU1535 strains, respectively (see Table 1).

TABLE 1

Fluctuation analysis of 5-FU-resistant cells in FU100 and FU1535[a]

|  | FU100 | FU1535 |
|---|---|---|
| $P_o$ METHOD[b] | $3.19 \times 10^{-7}$ | $2.86 \times 10^{-8}$ |
| MEAN METHOD[b] | $2.92 \times 10^{-7}$ | $2.94 \times 10^{-8}$ |
| AVERAGE MUTATION RATE | $3.06 \times 10^{-7}$ | $2.90 \times 10^{-8}$ |

[a]Fluctuation analysis obtained from 100 independent cultures for FU100 and 124 independent cultures for FU1535; mean number of $FU^R$ colonies per plate was 16.6 per $10^7$ cells for FU100 and 17.1 per $10^{8\ cells}$ for FU1535; $FU^R$ colonies from each independent culture were isolated for mutational analysis.
[b]Mutation rate estimates calculated as follows: $P_0$ Method (Luria, S. E., et al., (1943) Genetics 28: 491-511). - estimate based on ratio, $P_0$ of plates without colonies, $T = [(\ln 2)(-\ln P_0)]/(N)$, and Mean Method (Capizzi, R. L., et al., (1973) Mutation Res. 17: 147-148). - estimate based on the mean number of $FU^R$ colonies per culture, Cm = (CTN) ln(CTN); T = mutation rate, N = number of cells per plate, C = number of replicate plates, and m = mean number of colonies per plate.

The data presented in Table 1 further establishes that the presence of pKM101 in the FU100 indicator strain induces an elevated mutational burden. This is apparent from the observation that there is a 10-fold higher spontaneous mutation rate at the upp locus of the FU100 strain relative to the FU1535 strain. The two strains differ from each other only in the presence of the pKM101 plasmid in the FU100 but not the FU1535 strain. As indicated above, pKM101 provides an error-prone replicative bypass of DNA lesions and renders FU100 more susceptible to induced mutagenesis (Perry, K. L., et al., (1985) Proc. Natl. Acad. Sci. USA 82:4331-4335; Tang, M., et al., (1999) Proc. Natl. Acad. Sci. USA 96:8919-8924; and Koch, W. H, et al., (2000) Mutation Res. 457:1-13).

Two 5-FU-resistant clones were then isolated from each independent plate and used to elucidate the spontaneous mutational spectrum for each strain.

Example 3

$FU^R$ Clones Display Changes in the upp Gene and Determination of the Spontaneous Mutational Spectra of the upp Locus Upon determining the Salmonella upp and uraA nucleic acid sequences, several 5-FU-resistant clones were isolated and their genomic DNA sequenced to confirm their role in the biochemical pathway of 5-FU resistance. Genomic DNA was isolated from the 5-FU-resistant clones as described above, both the upp and uraA genes were amplified by PCR, and the resulting PCR products sequenced. 100% of the $FU^R$ clones analyzed contained molecular defects (i.e., sequence changes) in the upp gene, all of which altered the amino acid sequence of the protein. Indicating that upp is the target gene that is chiefly responsible for 5-FU resistance in Salmonella. All subsequent mutational studies focused solely on the upp target based on this observation.

The mutational spectra at the upp locus were determined by amplifying and sequencing the upp coding region for each 5-FU-resistant clone. Amplification of the upp coding sequence was performed directly from saturated bacterial cultures. Cell preps were prepared as follows: 5 ml of medium were inoculated with independent $FU^R$ clones isolated during fluctuation analysis, and grown to confluence overnight. 400 µl aliquots were removed, the bacteria pelleted by centrifugation, the supernatant removed and the cell pellet resuspended in 100 µl of water. This procedure was repeated three times. The cleansed cell pellet was resuspended in water and lysed by boiling for 10 minutes. After cooling 10 µl aliquots were removed from the boiled preparations and used directly in PCR.

The upp coding sequence was subsequently amplified using the PCR primers Sal upp Forward-1 (5' ATC CAG GTC AAG CAT ACA TTG TGT TG 3'(SEQ ID NO.: 18)) and Sal upp Reverse (%' CGA TAG CAC GGC GCG TCA T 3'(SEQ ID NO.: 19)). Both primers anneal approximately 75 bases from the upp start or stop codon respectively, resulting in an amplicon just over 800 bases in length.

PCR was performed in 10 mM Tris-HCL, pH 8.3, 50 mM KCl, 2.5 mM $MgCl_2$, 200 uM dNTPs, with 100 ng of each primer and 2.5 units TaqGOLD polymerase (Applied Biosystems). PCR was initiated by activating the Taq polymerase at 95° C. for 10 minutes, followed by 35 cycles of 95° C. for 15 seconds, 60° C. for 15 seconds, and 72° C. for 30 seconds. There was a final extension for minutes at 72 degrees C. All reactions were performed in a GeneAmp PCR System 9700 machine (Applied Biosystems). PCR products were visualized on an agarose gel, and full-length products were purified.

The molecular defect (e.g., mutation) was subsequently determined by automated sequencing.

The upp coding sequences from a total of 156 independent spontaneous 5-FU mutants were analyzed. Of these 42% were based on substitutions, 41% were frameshift mutations, and 17% were larger insertion or deletion mutations (see Table 2). A total of 169 independent spontaneous FU1535 spontaneous mutants were analyzed and found to consist of 43% base substitutions, 30% frameshift mutations, and 27% were larger insertion or deletion mutations (see Table 2).

TABLE 2

Summary of Spontaneous Mutations at the upp Locus in the FU100 and FU1535[a]

|  | FU100 | FU1535 |
|---|---|---|
| Base Substitutions | 66 (42) | 72 (43) |
| TRANSITIONS: |  |  |
| G:C → A:T | 14 (9) | 14 (8) |
| A:T → G:C | 8 (5) | 9 (5) |
| TRANSVERSIONS: |  |  |
| G:C → C:G | 6 (4) | 4 (2) |
| G:C → T:A | 25 (16) | 34 (20) |
| A:T → C:G | 4 (3) | 8 (5) |
| A:T → T:A | 9 (6) | 3 (2) |
| Frameshifts | 64 (41) | 51 (30) |
| +1 bp | 12 (8) | 16 (9) |
| −1 bp | 43 (28) | 32 (19) |
| −2 bp | 9 (6) | 3 (2) |
| Insertion[b] | 3 (2) | 10 (6) |
| Deletions[b] | 23 (15) | 36 (21) |
| Total Number of Mutants | 156 (100) | 169 (100) |

[a]Number of mutants (percent of total).
[b]Insertion or deletion mutations of 4 or more nucleotides; see Table 3.

A comparison of the spontaneous mutation spectra of the two strains indicates that the frequency of base substitutions are nearly identical. The FU100 strain showed a subtle increase in the frequency of frameshift mutations relative to the FU1535 strain; while insertion or deletion mutations were decreased in FU100 relative to FU1535. Frameshift mutations were defined as single or two-base frameshifts, predominantly occurring in repetitive sequences, and insertion or deletions mutations consisted of mutations of greater than or equal to four bases.

To calculate the relative mutation rates for specific mutational events, the incidence of a particular mutational event (Table 2) was multiplied by the mutation rate determined by fluctuation analysis (Table 1). These values (relative mutation rates) are presented in Table 4 for both strains. The data in Table 4 also provides the fold increases in the relative mutational rates for the FU100 strain relative to the FU1535 strain. With the overall mutation rate in the FU100 strain exhibiting a 10-fold incresase relative to the FU1535 strain, which can be attributed to the presence of the pKM101 plasmid, the fold increase values for individual mutation rates can be examined to determine the role of pKM101 on a particular mutational event.

The results indicate that approximately 40% of all of the mutations were base substitutions, present at the same relative percentage in both strains. Frameshift mutations also accounted for approximately 40% of the mutations; however their incidence was slightly elevated in FU100. The remaining mutations were larger insertions and deletions, which were slightly elevated in FU1535 (See Table 3).

TABLE 3

Summary of Spontaneous Insertion and Deletion Mutations at the upp Locus in the FU100 AND FU1535

| Mutation | Number of Bases | FU100[a] | FU1535[a] |
|---|---|---|---|
| Insertion[b] | 4-10 | 1 | 7 |
|  | 11-20 | 1 | 0 |
|  | 21-49 | 0 | 2 |
|  | >50 | 1 | 1 |
| Deletion[c] | 4-10 | 14 | 23 |
|  | 11-20 | 1 | 10 |
|  | 21-49 | 5 | 1 |
|  | >50 | 3 | 2 |

[a]Total number of upp mutants sequenced: FU100 = 156, FU1535 = 169.
[b]Insertion mutations - majority of smaller insertions less than 10 bases are duplications of repetitive sequences; all larger insertions are sequences of unknown origin; see FIG. 1 for locations.
[c]Deletion mutations - majority of smaller deletions are the loss of several bases in repetitive sequences; all large-scale deletions are non-specific loss of the coding sequence.

The FU100 muational spectra indicates that pkM101 significantly elevated the rate of all classes of mutation at the upp locus of this indicator strain. For base substitution mutations, pKM101 increased both G:C to A:T to A:T to G:C transition mutations at approximately the same level; however, it produced a profound effect on specific types of transversion mutations, which is evident from the 34-fold higher mutation rate for A:T to T:A mutations and a 17-fold increase in G:C to C:G mutations (See Table 4).

TABLE 4

Relative Spontaneous Mutation Rate Per Type of Mutation at the upp Locus in the FU100 AND FU1535[a]

|  | FU100 | FU1535 | Fold Increase[b] |
|---|---|---|---|
| Mutation Rate[c] (×10$^{-9}$) | 306.0 | 29.0 | 10.6 |
| Base Substitutions | 129.5 | 12.4 | 10.5 |
| Transitions: |  |  |  |
| G:C → A:T | 27.5 | 2.4 | 11.4 |
| A:T → G:C | 15.7 | 1.5 | 10.2 |
| Transversions: |  |  |  |
| G:C → C:G | 11.8 | 0.7 | 17.1 |
| G:C → T:A | 49.0 | 5.8 | 8.4 |
| A:T → C:G | 7.8 | 1.4 | 5.7 |
| A:T → T:A | 17.7 | 0.5 | 34.3 |
| Frameshifts | 125.5 | 8.8 | 14.3 |
| +1 bp | 23.5 | 2.7 | 8.6 |
| −1 bp | 84.3 | 5.5 | 15.4 |
| −2 bp | 17.7 | 0.5 | 34.3 |
| Insertion | 5.9 | 1.7 | 3.4 |
| Deletions | 45.1 | 6.2 | 7.3 |

[a]Mutation rate multiplied by the incidence of each type of mutation presented in Table 2 to obtain relative mutation rates per type of mutation (×10$^{-9}$).
[b]Fold increase of FU100 relative to FU1535.
[c]Mutation rate estimate obtained by fluctuation analysis; see Table 1.

The data summarized in Table 4 suggests that the presence of pKM101 confers a bias for particular types of mutations, or more specifically the mutational specificity of the error-prone polymerase encoded by the plasmid accounts for these types of transversions.

The rate of frameshift mutations were also increased significantly by pKM101, illustrating its contribution to these mutations. For example, the rate of −2 base frameshifts was 34-fold higher in FU100 relative to FU1535. Larger insertion and deletion mutations were increase to a lesser extent by pKM101, increasing only three fold and seven fold respectively. It can be concluded that pKM101 significantly enhanced the spontaneous rates of all classes of mutations at the upp locus, with more profound effects on A:T and T:A transitions and −2 base frameshifts, and only a moderate effect on insertion and deletion mutations (Table 4).

Considered together the mutational spectra at the upp locus reveal 147 mutable sites, representing approximately 23% of the total 627-base coding sequence. Approximately 55% of all mutations from both strains were frameshift, deletion, or insertion mutations, 25% consisted of missense mutations, 15% were nonsense mutations, and the remaining 5% were observed in the promoter region. This data suggests that as a mutational target the upp gene can detect a diverse spectrum of mutagenic events, making it an ideal candidate for use as the basis of a forward mutation assay.

Example 4

Forward Mutation Assay

FU100 Indicator Strain

The Ames *Salmonella typhimurium* strain TA100 (hisG46, rfa, ΔuvrB, pKM101) was kindly provided by Dr. B. N. Ames, Biochemistry Department, University of California, Berkeley, Calif. A spontaneous his+ revertant of the TA100 strain was isolated on minimal medium. A 5-fluorouridine-resistant clone (5-FUR$^R$) was then isolated by selecting approximately $10^6$ his+ bacteria on a minimal medium plate containing 0.2 μg/ml 5-fluorouridine to minimize cross feeding during 5-FU selection. This strain was designated FU100 (his+, rfa, ΔuvrB, pKM101, and was 5-FUR$^R$) used in all subsequent experiments. Tests for the presence of uvrB, rfa, and pKM101 were performed to confirm the genotype of FU100 (3).

Preparation of Frozen Stock Vials 100 tubes containing 5 mL of MinE medium (0.2 mg/ml $MgSO_4 \cdot 7 H_2O$, 2.0 mg/ml citric acid-$H_2O$, 20 mg/ml D-(+) glucose; 3.5 mg/mi $NaNH_4HPO_4 \cdot 4 H_2O$, 10 mg/ml $K_2HPO_4$; 12.2 μg/ml d-biotin) (McCann, J., et al., (1975) *Proc. Natl. Acad. Sci. USA* 72:5135-9), supplemented with 2 mg/ml casamino acids and 5 μg/ml ampicillin, were each inoculated with approximately $10^4$ FU100 bacteria and incubated at 37° C. on a rotary wheel until saturation density was reached. A 10 μl sample from each tube was plated on MinE plates containing 2.0 μg/ml 5-FU and incubated overnight at 37° C. to determine the number of 5-FU resistant mutants present. Tubes were held at 4° C. during the incubation. 60 tubes with the fewest 5-FU resistant mutants were selected. Cells were resuspended in fresh medium, incubated for 3 hours at 37° C., and then pooled and frozen as 1-mL aliquots in MinE medium with 10% dimethyl sulfoxide.

Assay Protocol

For each mutation experiment, two frozen 1-ml aliquots of FU100 were quickly thawed in a 37° C. water bath, pelleted by centrifugation, washed to remove the DMSO, and suspended in 35 mL of MinE medium. The culture was shaken for approximately 1 hour at 37° C. until the optical density at 600 nm ($OD_{600}$) reached the target density of 0.3. A 16-ml aliquot of culture was added to each of two 50-ml tubes containing 3.6 ml of a NADPH-generating system (5.6 mM glucose-6-phosphate, 4.5 mM NADP+, 5 mM sucrose, 110 mM $Na_2HPO_4$, 37 mM KCl, and 9 mM $MgCl_2$) and either 0.4 ml rat liver S-9 or an equal volume of sodium phosphate buffer. Aliquots of these mixtures were distributed into three 12-well cluster dishes (one for exposure with S-9, one for exposure without S-9, one for controls with and without S-9), and exposed to test compounds as 1-ml aliquots for 2 hour as outlined in FIG. 1.

Following treatment, the 1-ml aliquots were transferred into 9 ml of warm MinE medium in a 50 ml tube and incubated at 37° C. on a rotary wheel for 3 hours. Next, 20 ml of medium was added to each culture tube and 0.25 ml aliquots were transferred to a 96-well plate for $OD_{600}$ measurements to assess toxicity (OD Day 1). OD measurements were obtained using a SPECTRAmax plus$^{384}$ microplate spectrophotometer (Molecular Devices Corporation, Sunnyvale, Calif.). Bulk cultures were then incubated overnight in the dark at 30° C. to permit recovery from toxicity and to allow time for the test cells to express the $FU^R$ phenotype.

The next day, $OD_{600}$ was again assessed to adjust cell number plated on 5-FU plates (OD Day 2; 100 μl of the culture diluted with 150 μl MinE medium for $OD_{600}$ measurements). For plating, a 35 μl aliquot of each culture was added to 31.4 mL of MinE medium with 2 μg/ml of 5-FU and 10 μg/ml of bromcresol purple. The mixture was then dispersed into a 384-well plate (75 μl/well) and placed at 37° C. for 3 days in a humidified incubator. Positive (yellow) wells containing 5-FU-resistant colonies were detected and enumerated by measuring the absorbance at 422 nm on a SPECTRAmax Plus$^{384}$ microplate spectrophotometer.

The data obtained for both survival (OD day 1), relative number of cells plated (OD day 2), and number of positive wells were imported into an Excel template. The adjusted mutants/well were calculated as follows: −ln [(384−no. positive wells)/(384)]/(OD day 2). A positive or induced response was considered significant if it exceeded four standard deviations above the historical background level (Table 8) and survival was greater than 5% (based on OD day 1).

Example 5

Optimization of Growth and Selective Culture Conditions

The growth rate of TA100 his+ in MinE at 37° C. was found to be slow when culturing in MinE medium. Since a faster rate would facilitate the performance of the assay, the effects of casamino acids (CAA) supplementation on the growth rate was investigated. Culture growth was measured by optical density over a wide range of CAA concentrations. A significant enhancement of growth was observed using 0.2% CAA and above (data not shown). 0.2% CAA was chosen as a standard supplement to MinE medium in all subsequent studies.

A similar study was then conducted to determine the optimal concentration of the selective agent 5-FU. The growth rate was determined for cultures in MinE containing up to 8 μg/ml 5-FU. Cultures containing less than or equal to 0.5 μg/ml continued to grow, albeit at longer doubling times as the concentration increased, while those with greater than or equal to 1 μg/ml 5-FU significantly inhibited culture growth (data not shown). The concentration of 2 μg/ml 5-FU was chosen for selection of 5-FU-resistant clones in subsequent mutation assays.

Since reducing the background mutant frequency would increase assay sensitivity, experiments were undertaken to identify factors affecting background rate. The effects of room light and culture temperature were investigated. Significant elevation in the spontaneous mutation frequency was observed for cultures grown under ambient fluorescent light relative to that observed for cultures grown in the dark (data not shown). Therefore, it is imperative that cultures are kept in the dark as much as possible during the preparation of stock frozen aliquots and during an actual experiment. With cultures grown in the dark, the incubation temperature (room temperature, 30° C., or 37° C.) had little to no effect on background mutant frequency (data not shown).

Example 6

The Use of 5-fluorouridine Resistant Tester Strains Increases the Plating Efficiency of FU$^R$ Mutants Initial experiments revealed that the presence of wild-type TA100 his+ cells decreased the plating efficiency of FU$^R$ mutants in 5-FU both on agar plates and in 384 microtiter dishes, resulting in a decrease in apparent mutation frequency as a function of the number of cells plated. It was surmised that 5-fluorouridine produced in wild-type cells (formed by dephosphorylating 5-fluorouridine monophosphate after the phosphoribosylation of 5-FU) could diffuse into the medium and could be taken up by FU$^R$ mutants. In the mutants 5-fluorouridine could be converted back to the toxic monophosphate form by uridine kinase.

To circumvent this toxic cross feeding, several clones of TA100 his+ were selected that were resistant to 0.2 µg/ml 5-fluorouridine while also retaining sensitivity to 5-FU (approximately 12.5% of all 5-fluorouridine resistant mutants were also resistant to 5-FU). The data summarized in Table 5 establishes that the 5-fluorouridine resistant mutants (FUR$^R$) displayed a stable mutation frequency as a function of cells when they were plated when on agar plates in the presence of 5-FU (see, Table 5). Thus, the data provided herein indicated the advantage of using 5-fluorouridine resistant tester strains.

TABLE 5

Effect of cell concentration on 5-FU mutant frequency in TA100 and in 5-FU-resistant clones of TA100

| Strain[a] | Cells per Plate | Total FU$^R$ Colonies[b] |
|---|---|---|
| TA100 (his+) | $1 \times 10^5$ | 2 |
|  | $1 \times 10^6$ | 11 |
|  | $1 \times 10^7$ | 32 |
| Clone 1 | $1 \times 10^5$ | 1 |
|  | $1 \times 10^6$ | 16 |
|  | $1 \times 10^7$ | 111 |
| Clone 2 | $1 \times 10^5$ | 1 |
|  | $1 \times 10^6$ | 27 |
|  | $1 \times 10^7$ | 213 |
| Clone 3 | $1 \times 10^5$ | 2 |
|  | $1 \times 10^6$ | 34 |
|  | $1 \times 10^7$ | 405 |
| Clone 4 | $1 \times 10^5$ | 4 |
|  | $1 \times 10^6$ | 25 |
|  | $1 \times 10^7$ | 256 |

[a]TA100 sensitive to 5-fluorouridine; all clones 1-4 are resistant to 5-fluorouridine; clone 2 was used for all future studies and designated FU100.
[b]FU$^R$ colonies on 100-mm plates; total number of colonies on 5 plates.

Similar results were obtained when 384-well dishes were used for plating (see Table 6). Thus, it was concluded that the use of 5-fluorouridine-resistant strains avoided toxic cross feeding. One of the 5-fluorouridine-resistant clones was chosen (Clone #2), designated FU100, and used for all subsequent studies, including the validation study summarized in Example 9.

TABLE 6

Effect of cell concentration on 5-FU mutant frequency in TA100 and in FU100, a 5-fluorouridine-resistant clone of TA100, in 384-well plates

| Strain[a] | Cells per Well | Total Positive Wells[b] | Apparent Mutant Frequency[c] ($\times 10^{-6}$) |
|---|---|---|---|
| TA100 | $3 \times 10^3$ | 0 | 0.9[d] |
|  | $1 \times 10^4$ | 6 | 6.3 |
|  | $3 \times 10^4$ | 11 | 3.9 |
|  | $1 \times 10^5$ | 10 | 1.1 |
|  | $3 \times 10^5$ | 2 | 0.1 |
|  | $1 \times 10^6$ | 26 | 0.3 |
| FU100 | $3 \times 10^3$ | 1 | 3.5 |
|  | $1 \times 10^4$ | 3 | 3.1 |
|  | $3 \times 10^4$ | 19 | 6.9 |
|  | $1 \times 10^5$ | 57 | 7.0 |
|  | $3 \times 10^5$ | 109 | 5.6 |
|  | $1 \times 10^6$ | 183 | 6.1 |

[a]TA100 - 5-fluorouridine-sensitive; FU100 - 5-fluorouridine-resistant Clone 2 (see Table 5).
[b]Total number of FU$^R$ colonies (positive wells) per 384-well plate at each cell concentration.
[c]Apparent mutant frequency = (positive wells)/(cells per well × 384 wells).
[d]Calculated using 1 for the number of positive wells.

Example 7

The Effects of Overnight Grow-Back on the Plating Efficiency of FU$^R$ Mutants

Initial experiments revealed that with certain mutagens the plating efficiency of FU$^R$ mutants in a treated culture could be significantly suppressed at the end of day 1, even though the culture may have achieved a similar OD$_{600}$ relative to the untreated control. Methylmethane sulfonate and 2-nitrofluorene are examples of compounds that display this phenomenon. To remedy this decrease in plating efficiency of FU$^R$ mutants, an overnight grow back was introduced into the assay. Cultures were diluted 3-fold and grown overnight at three temperatures (25° C., 30° C., and 37° C.).

Cultures incubated overnight at 37° C. did not fully recover the FU$^R$ mutant plating efficiency, and also demonstrated a significant S-9 related toxicity (data not shown). The overnight incubation at 30° C., however, provided good viability, rate of growth, and recovery of mutant plating efficiency. The data provided in FIG. 5 demonstrates the effect of an overnight grow back on the plating efficiency of FU$^R$ mutants for assays evaluating the genotoxicity of methylmethane sulfonate and 2-nitrofluorene. Based on these observations, an overnight grow-back at 30° C. was subsequently incorporated into the optimized 5-FU assay protocol.

Example 8

The Effect of 5-Fluoroorotic Acid on the Sensitivity of the 5-FU Assay

Alternative Method for Preparing Frozen Stocks with a Lower FU$^R$ Background

It has been determined that frozen stocks with a lower FU$^R$ background can be prepared by growing bulk cultures with 5-fluoroorotic acid and uracil prior to freezing. Briefly, cultures were grown in MinE without CAA, and supplemented with 50 µg/ml 5-fluoroorotic acid, 20 µg/ml uracil and 5 µg/ml ampicillin. Following an overnight incubation, the bacteria were pelleted, washed once in MinE, and resuspended in the initial volume with fresh MinE medium. The culture was then incubated for an additional 2.5 hr. The cells were pelleted and resuspended in half the initial volume of MinE+10% DMSO (final $OD_{600}$ approximately 2.2) and aliquots frozen in liquid nitrogen.

Use of these "cleansed" frozen vials under standard FU Assay conditions resulted in lower control mutant frequencies. Controls values were reduced from an average of 0.25 adjusted mutants per well without S9 and 0.20 with S9 (average of 160 and 120 wells per 384-well plate, respectively) to an average of 0.11 adjusted mutants per well without S9 and 0.11 with S9 (average of 90 and 80 wells per 384-well plate, respectively) when "cleansed" frozen cultures were used (Table 8). It should be noted that the reduction in background mutant frequency seen under actual assay conditions was not as profound as that observed in cultures grown in the presence of 5-fluoroorotic acid and uracil, suggesting that most of the mutants scored in the 5-FU Assay are generated during the conduct of the assay.

The method of preparing "cleansed" frozen vials with 5-fluoroorotic acid and uracil was not implemented until greater than half of the validation compounds had been tested. The compounds screened with these stocks are indicated in Table 9. Since the 5-FU Assay had detected all of potentially positive compounds using frozen stocks without a reduced background (see Table 5), most of these compounds were not repeated with these new frozen stocks.

Example 9

Validation of the 5-FU Assay

The optimized 5-FU Assay protocol is illustrated in FIG. 4. The results of the validation study indicate that the 5-FU Assay can be validated with a wide variety of mutagens and non-mutagens. More specifically, the data provided herein indicates that the disclosed assay detects a wide variety of mutagens, including highly toxic compounds that are usually problematic in the standard Ames assay.

Table 7 lists the test compounds used to validate the optimized 5-FU assay illustrated in FIG. 4.

TABLE 7

Chemicals tested in 5-FU assay using FU100

| Chemical | CAS No. | Supplier[a] | Solvent[b] | Dose Range (μg/ml) |
|---|---|---|---|---|
| 9-Aminoacridine•HCl•H$_2$O | 52417-22-8 | A | D | 1-500 |
| 2-Aminoanthracene | 613-13-8 | A | D | 0.02-10 |
| 2-Amino-5-nitrophenol | 121-88-0 | A | D | 1-500 |
| 5-Azacytidine | 320-67-2 | A | D | 1-500 |
| Benzaldehyde | 100-52-7 | A | D | 10-5000 |
| Benzo[a]pyrene | 50-32-8 | S | D | 0.04-20 |
| Benzyl Alcohol | 100-51-6 | S | D | 10-5000 |
| Benzyl Chloride | 100-44-7 | A | D | 10-5000 |
| Butylated Hydroxyanisole | 25013-16-5 | S | D | 1-500 |
| 1-Chloro-2-propanol | 127-00-4 | A | W | 10-5000 |
| Coumarin | 91-64-5 | A | D | 10-5000 |
| Cumene Hydroperoxide | 80-15-9 | A | D | 10-5000 |
| Cyclophosphamide•H$_2$O | 6055-19-2 | S | W | 3-1500 |
| 2,4-Dichlorophenol | 120-83-2 | S | D | 0.1-50 |
| Dicumyl peroxide | 80-43-3 | A | D | 10-5000 |
| Di(2-ethylhexyl) phthalate | 117-81-7 | A | D | 10-5000 |

TABLE 7-continued

Chemicals tested in 5-FU assay using FU100

| Chemical | CAS No. | Supplier[a] | Solvent[b] | Dose Range (μg/ml) |
|---|---|---|---|---|
| Diethylstilbestrol | 56-53-1 | S | D | 2-1000 |
| Dimethyl Sulfoxide | 67-68-5 | A/S | W | 10-5000 |
| 1,2-Epoxybutane | 106-88-7 | A | D | 10-5000 |
| Ethylene Glycol | 107-21-1 | S | D | 10-5000 |
| Hydrogen Peroxide | 7722-84-1 | S | W | 0.5-300 |
| 8-Hydroxyquinoline | 148-24-3 | A | D | 0.3-150 |
| ICR-191 | 17070-45-0 | S | D | 0.02-10 |
| Isobutyl Nitrite | 542-56-3 | A | D | 10-5000 |
| Lithocholic Acid | 434-13-9 | S | D | 4-2000 |
| Menthol | 89-78-1 | A | D | 1-500 |
| 20-Methylcholanthrene | 56-49-5 | S | D | 0.1-50 |
| Methyl methanesulfonate | 66-27-3 | A | D | 0.2-100 |
| 2-Nitrofluorene | 607-57-8 | A | D | 0.004-2 |
| Nitrofurantoin | 67-20-9 | S | D | 0.1-50 |
| p-Nitrophenol | 100-02-7 | S | D | 1-500 |
| 4-Nitroquinoline N-oxide | 56-57-5 | A | D | 0.001-0.5 |
| N-Nitrosodimethylamine | 62-75-9 | S | W | 4-2000 |
| N-Nitroso-N-methylurea | 684-93-5 | S | D | 1-500 |
| Phenobarbital | 50-06-6 | M | W | 10-5000 |
| Phenol | 108-95-2 | A | D | 10-5000 |
| Proflavine HCl | 952-23-8 | A | W | 0.1-50 |
| Reserpine | 50-55-5 | S | D | 3-1500 |
| Saccharin | 82385-42-0 | S | W | 10-5000 |
| Safrole | 94-59-7 | S | D | 1-500 |
| Sodium Azide | 26628-22-8 | S | W | 1-500 |
| Sodium Dodecyl Sulfate | 151-21-3 | F | W | 4-2000 |
| Tamoxifen | 10540-29-1 | S | D | 0.1-50 |
| Tetracycline HCl | 64-75-5 | A | W | 0.02-10 |
| Wyeth 14,643 | 50892-23-4 | C | D | 10-5000 |

[a]Supplier: A—Aldrich; S—Sigma; M—Merck; F—Fisher; C—Chemsyn Science.
[b]Chemical solvent: D—DMSO; W—Water.

Table 8 summarizes the criteria for positive result in 5-FU assay using the FU100 tester strain described and claimed herein. Briefly, the criteria for positive responses included an elevation in adjusted mutants/well that was greater than or equal to 4 standard deviations above the historical mean in cultures with greater than or equal to 5% survival on Day 1 (Table 8). A positive compound was defined when two or more doses met the aforementioned criteria. Weakly positive compounds exhibited only one positive dose, and were confirmed by repeating the assay.

TABLE 8

Criteria for positive result in 5-FU assay using FU100

| S9 Activation[a] | Statistic | Adjusted Mutants/well Without Background Reduction[b] | Adjusted Mutants/well With Background Reduction[c] |
|---|---|---|---|
| −S9 | Control Mean | 0.253 | 0.114 |
| | Control Std Dev | 0.019 | 0.020 |
| | Positive Threshold[d] | 0.330 | 0.194 |

TABLE 8-continued

Criteria for positive result in 5-FU assay using FU100

| S9 Activation[a] | Statistic | Adjusted Mutants/ well Without Background Reduction[b] | Adjusted Mutants/well With Background Reduction[c] |
|---|---|---|---|
| +S9 | Control Mean | 0.197 | 0.107 |
|  | Control Std Dev | 0.030 | 0.021 |
|  | Positive Threshold[d] | 0.317 | 0.191 |

[a]Values from control samples incubated either in the presence of S9 activation (+S9) or without S9 activation (−S9).
[b]Average adjusted mutants per well in control samples without the background mutation frequency reduced; adjusted mutants per well = −ln ((384-positive wells)/384), then normalized for cell number plated; the average number of $FU^R$ colonies (positive wells) per 384-well plate was 160 without S9 and 120 with S9.
[c]Average adjusted mutants per well in control samples with the background mutation frequency reduced; adjusted mutants per well = −ln ((384-positive wells)/384), then normalized for cell number plated; the average number of $FU^R$ colonies (positive wells) per 384-well plate was 90 without S9 and 80 with S9.
[d]Positive threshold = (control mean adjusted mutants per well) + (4 × std dev).

Among the compounds used for validating the 5-FU Assay were a series of compounds previously tested by Gee, et al. (Gee, P., et al., (1998) *Mutation Res.* 412:115-130). These compounds were identified as agents that posed a detection challenge to the standard Ames assay. In general, these mutagens appeared to be toxic to *Salmonella* in the concentration range required for increases in mutation rate. In addition, several toxic non-mutagens used previously in the validation of other genetic toxicology assays (Storer, R. D., et al., (1996) *Mutation Res.* 368:59-101) were chosen to ensure that the 5-FU Assay did not generate false positives as a result of high toxicity.

Figure 6:
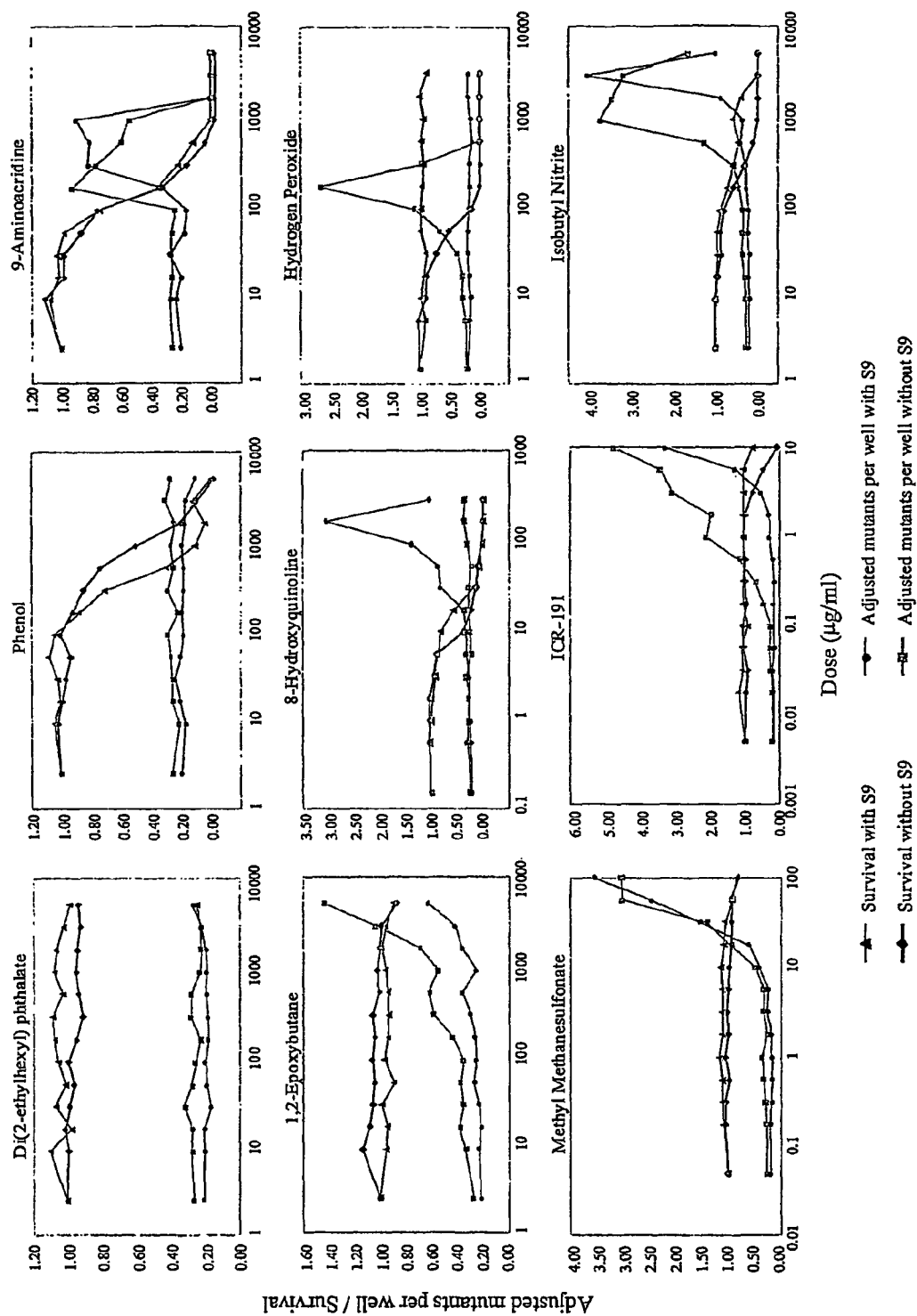
FIGS. 6A through 6I are a series of line graphs which provide representative 5-FU Assay results from several compounds. Test samples were treated according to the experimental protocol presented in FIG. 1 either with or without S9. Both survival and adjusted mutants per well are presented for both treatment groups (▲—survival with S9; ♦—survival without S9; ●—adjusted mutants per well with S9; ■—adjusted mutants per well without S9). The data includes representative negative/non-toxic compounds [di(2-ethylhexyl) phthalate], negative/toxic compounds (phenol), positive compounds in non-toxic concentrations (methylmethane sulfonate, ICR-191, and 1,2-epoxybutane), and positive compounds in toxic concentrations (9-aminoacridine, 8-hydroxyquinoline, hydrogen peroxide, and isobutyl nitrite).

Table 9 provides a summary of the validation results produced in forward mutation assays using the FU100 tester strain disclosed and claimed herein. In total, 45 compounds were tested, consisting of 25 known mutagens and 20 non-mutagens. All of the results obtained in the 5-FU assay correlated 100% with the data collected using the battery of standard Ames reversion strains. More specifically, positive results were obtained for all known mutagens including those with detection challenges in the standard Ames assay, demonstrating the sensitivity of the assay for detecting mutagenic compounds. All non-mutagens, including several that have been characterized as being extremely toxic, yielded a negative response in the 5-FU assay (See FIG. 6 and Table 9).

TABLE 9

Summary of validation, results in 5-FU assay using FU100

| Chemical[a] (NTP Results) | S9 Activation[b] | Results[c] | Lowest Positive Dose[d] (μg/ml) | LD50[e] (μg/ml) |
|---|---|---|---|---|
| 9-Aminoacridine•HCl•H₂O | − | Pos | 16 | >9 |
| (SA+, CA+, SC+) | + | Pos | 16 | >9 |
| 2-Aminoanthracene | − | Pos | 0.6 | >10 |
| (SA+, CA?, SC+) | + | Pos | 0.2 | >2 |
| 2-Amino-5-nitrophenol | − | Pos | 2.8 | >300 |
| (SA+, CA+, SC+, ML+) | + | Neg | — | >150 |
| 5-Azacytidine | − | Pos | 0.9 | >3 |
| (SA+, CA+, SC+, ML+, MN+) | + | Pos | 2.8 | >5 |
| Benzaldehyde | − | Neg | — | >150 |
| (SA−, CA−, SC+, ML+) | + | Neg | — | >150 |
| Benzo[a]pyrene | − | Neg | — | >20 |
| (SA+, CA+, SC+, ML+) | + | Pos | 0.4 | >20 |
| Benzyl Alcohol* | − | Neg | — | >900 |
| (SA−, CA+, SC+[w], ML?) | + | Neg | — | >500 |
| Benzyl Chloride | − | Pos | 28 | >1500 |
| (SA+[w], CA+, SC+, ML+) | + | Pos | 50 | >150 |
| Butylated Hydroxyanisole* | − | Neg | — | >30 |
| (SA−, MN−) | + | Neg | — | >30 |
| 1-Chloro-2-propanol | − | Pos[w] | 2800 | >2800 |
| (SA+, CA+, SC+) | + | Neg | — | >900 |
| Coumarin | − | Neg | — | >900 |
| (SA+, CA+[w], SC+, MN−) | + | Pos | 50 | >150 |
| Cumene Hydroperoxide | − | Pos | 16 | >90 |
| (SA+) | + | Pos | 160 | >300 |
| Cyclophosphamide•H₂O | − | Neg | — | >1500 |
| (SA+, CA+, SC+, MN+) | + | Pos[w] | 1500 | >300 |
| 2,4-Dichlorophenol* | − | Neg | — | >50 |
| (SA?, CA−, SC+, ML+) | + | Neg | — | >30 |
| Dicumyl peroxide | − | Neg | — | >5000 |
| (SA−) | + | Neg | — | >5000 |
| Di (2-ethylhexyl) phthalate* | − | Neg | — | >5000 |
| (SA−, CA−, SC+−?, ML−, MN?) | + | Neg | — | >5000 |
| Diethylstilbestrol* | − | Neg | — | >100 |
| (SA−, CA+, SC−, ML+) | + | Neg | — | >60 |
| Dimethyl Sulfoxide | − | Neg | — | >5000 |
| (SA−, CA−, SC−) | + | Neg | — | >5000 |
| 1,2-Epoxybutane | − | Pos | 8.9 | >5000 |
| (SA+, CA+, SC+, ML+, MN−) | + | Pos | 500 | >5000 |
| Ethylene Glycol* | − | Neg | — | >5000 |
| (SA−, CA−, SC−, ML−) | + | Neg | — | >5000 |
| Hydrogen Peroxide[f] | − | Pos | 3 | >5 |
| (SA+[w]) | + | Neg | — | >300 |
| 8-Hydroxyquinoline | − | Neg | — | >3 |
| (SA+, CA+[w], SC+, ML+, MN−) | + | Pos | 5 | >8 |
| ICR-191[g] | − | Pos | 0.2 | >3 |
| (SA+) | + | Pos | 3.2 | >10 |

TABLE 9-continued

Summary of validation, results in 5-FU assay using FU100

| Chemical[a] (NTP Results) | S9 Activation[b] | Results[c] | Lowest Positive Dose[d] (μg/ml) | LD50[e] (μg/ml) |
|---|---|---|---|---|
| Isobutyl Nitrite | − | Pos | 28 | >160 |
| (SA+, CA+, SC+, MN+) | + | Pos | 500 | >900 |
| Lithocholic Acid* | − | Neg | — | >2000 |
| (SA−, CA−, SC−, ML+) | + | Neg | — | >2000 |
| Menthol*[h] | − | Neg | — | >16 |
| (SA−, CA−, SC−, ML−, MN−) | + | Neg | — | >9 |
| 20-Methylcholanthrene | − | Pos | 5 | >50 |
| (SA+, CA−, SC+) | + | Pos | 0.2 | >50 |
| Methyl Methanesulfonate | − | Pos | 0.6 | >100 |
| (SA+) | + | Pos | 10 | >100 |
| 2-Nitrofluorene | − | Pos | 0.02 | >1 |
| (SA+) | + | Pos | 0.6 | >2 |
| Nitrofurantoin | − | Pos | 0.1 | >1 |
| (SA+, CA+, SC+, ML+, MN−) | + | Pos | 0.1 | >1 |
| p-Nitrophenol* | − | Neg | — | >50 |
| (SA−, CA+, SC−) | + | Neg | — | >50 |
| 4-Nitroquinoline N-oxide | − | Pos | 0.01 | >0.5 |
| (SA+, CA+, SC+, ML+) | + | Pos[w] | 0.5 | >0.5 |
| N-Nitrosodimethylamine | − | Neg | — | >2000 |
| (SA+, CA+, SC+) | + | Pos | 360 | >2000 |
| N-Nitroso-N-methylurea[g] | − | Pos | 5.0 | >90 |
| (SA+) | + | Pos | 5.0 | >90 |
| Phenobarbital* | − | Pos[w] | 2800 | >500 |
| (SA+[w], CA+, SC−, ML+) | + | Pos[w] | 1500 | >500 |
| Phenol | − | Neg | — | >900 |
| (SA−, CA+, SC+, ML+) | + | Neg | — | >300 |
| Proflavine HCl | − | Pos[w] | 16 | >10 |
| (SA+) | + | Pos | 0.1 | >10 |
| Reserpine* | − | Neg | — | >1500 |
| (SA−, CA+−, SC−, ML−, MN−) | + | Neg | — | >1500 |
| Saccharin*[h] | − | Neg | — | >5000 |
| (SA−) | + | Neg | — | >5000 |
| Safrole* | − | Neg | — | >60 |
| (SA−, CA−, SC+ ML+) | + | Neg | — | >50 |
| Sodium Azide | − | Pos[w] | 160 | >50 |
| (SA+, CA−, SC+) | + | Pos[w] | 90 | >30 |
| Sodium Dodecyl Sulfate | − | Neg | — | >20 |
| (SA−, CA−, SC−, ML−) | + | Neg | — | >35 |
| Tamoxifen*[i] | − | Neg | — | >3 |
| (SA−) | + | Neg | — | >15 |
| Tetracycline HCl | − | Neg | — | >0.1 |
| (SA−, CA−, SC−, ML?) | + | Neg | — | >0.1 |
| Wyeth 14,643*[j] | − | Neg | — | >900 |
| (SA−) | + | Neg | — | >900 |

[a]Chemicals tested in 5-FU Assay; asterisk (*) indicates compounds tested using stock cultures with the background mutant frequency reduced (see Materials and Methods); NTP in vitro genetic toxicology test results: SA = Salmonella, CA = chromosome aberrations, SC = sister chromatid exchange, ML = mouse lymphoma, MN = micronucleus; + positive, +[w] weak positive, − negative, ? ambiguous (NTP Results Report 12 Aug. 2002).
[b]Chemical exposure either in the presence of S9 activation (+) or without S9 activation (−).
[c]Result measured in 5-FU assay based on criteria in Table 4: Pos = positive, Pos[w] = weak positive, Neg = negative.
[d]Lowest chemical dose tested that resulted in a positive response.
[e]LD50 defined as the dose that produced less than 50% survival on Day 1; dose listed was the approximate LD50, and is represented by the first dose that resulted in greater than 50% survival.
[f]Hydrogen peroxide results not available in NTP Results Report; data from Reference (Kenese, L. L., et al., (1989) Teratog. Carcinog. Mutagen. 9: 211-8).
[g]ICR-191 and N-Nitroso-N-methylurea results not available in NTP Results Report; data from Reference (McCann, J., et al., (1975) Proc. Natl. Acad. Sci. USA 72: 5135-9).
[h]Menthol and saccharin data listed in NTP Results Report are for different CAS numbers.
[i]Tamoxifen results not available in NTP Results Report; data from Reference (Gupta, S., et al., (1999) Mutation Res. 445: 1-8).
[j]Wyeth 14,643 results not available in NTP Results Report; data from Reference (Glauert, H. P., et al., (1984) Cancer Lett. 24: 147-56).

While the invention has been described in detail with reference to certain preferred embodiments thereof, it will be understood that modifications and variations are within the spirit and scope of that which is described and claimed.

Summary of Sequences

SEQ ID NO.: 1 (Genbank Accession AF427145) sets forth the nucleotide sequence of 2520-nucleobases that encodes a Salmonella typhimurium derived uracil transport protein (uraA protein) and the Uracil Phosphoribosyl Transferase protein (upp/UPRT). The coding portion for the uraA is defined by nucleotides 929-2218 (SEQ ID NO.: 5), while the coding region of the UPRT gene is defined by nucleotides 215-841 (SEQ ID NO.: 4).

SEQ ID NO.: 2 (FIG. 2) provides the deduced amino acid sequence of the Uracil phosphoribosyltransferase protein.

SEQ ID NO.: 3 (FIG. 3) provides the deduced amino acid sequence of the Uracil Transport Protein.

SEQ ID NO.: 6-20 provides oligonucleotide sequences for primers used to perform the cloning/amplification experiments described in this disclosure.

What is claimed:

1. A method for evaluating the genotoxic activity of a test compound comprising the steps of:
   a) providing microbial indicator cells that are 5-fluorouridine resistant (5-FUR$^R$) at a desired cell density;
   b) preparing a test compound for evaluation which may optionally include exposing the test compound to a metabolic activation system;
   c) preparing a test sample comprising the test compound of b) and the microbial indicator cells;
   d) incubating the test sample under conditions that promote the growth of the indicator strain;
   e) evaluating the toxicity of the test compound;
   f) incubating the test sample overnight under conditions that promote the growth of the indicator strain and expression of FU$^R$ phenotypes;
   g) exposing the test sample to a selective concentration of 5-Fluorouracil (5-FU); and
   h) determining the presence and number of 5-FU-resistant mutant indicator cells present in the test sample
   wherein the presence of 5-FU-resistant indicator cells indicates that the test compound has genotoxic activity.

2. The method of claim 1 wherein the microbial indicator cells are *Salmonella typhimurium* cells.

3. The method of claim 2 wherein the microbial indicator cells are derived from Ames TA100 indicator cells such that the cells are histidine independent (his$^+$) and 5-fluorouridine-resistant (5-FUR$^R$).

4. A method for evaluating the genotoxic activity of a test compound comprising the steps of:
   a) providing recombinant bacterial indicator cells that are 5-fluorouridine resistant at a desired cell density;
   b) preparing a test compound for evaluation which may optionally include exposing the test compound to a metabolic activation system;
   c) preparing a test sample comprising the test compound of b) and the microbial indicator cells;
   d) incubating the test sample under conditions that promote the growth of the indicator strain;
   e) evaluating the toxicity of the test compound;
   f) incubating the test sample overnight under conditions that promote the growth of the indicator strain and expression of FU$^R$ phenotypes;
   g) exposing the test sample to a selective concentration of 5-Fluorouracil (5-FU); and
   h) determining the presence and number of 5-FU-resistant mutant indicator cells present in the test sample
   wherein the presence of 5-FU-resistant indicator cells indicates that the test compound has genotoxic activity.

5. The method of claim 4 wherein the bacterial indicator cells are resistant to 0.2 ug/ml 5-fluorouridine.

6. The method of claim 4 wherein the bacterial indicator cells are further characterized by comprising a defective DNA repair system.

7. The method of claim 4 wherein the bacterial indicator cell comprises an error-prone DNA polymerase present on the pKM101 plasmid.

8. The method of claim 4 wherein the bacterial indicator cell comprises a mutation which facilitates transport of large compounds in the indicator cells.

9. The method of claim 1 wherein the metabolic activation system comprises a mammalian liver homogenate or extract.

10. The method of claim 9 wherein the metabolic activation system comprises a mammalian S9 preparation.

11. The method of claim 1 wherein the selective concentration of 5-FU is at least 1 ug/ml but not greater than 10 ug/ml.

12. The method of claim 11 wherein the selective concentration of 5-FU is at 2 ug/ml.

13. The method of claim 1 wherein the microbial indicator cells are prepared from a frozen stock of cells that is pre-treated by growing the cells in the presence of 5-fluoroorotic acid and uracil prior to preparing the frozen stock.

14. The method of claim 1 wherein the test sample is incubated overnight at 30° C.

15. The method of claim 1 wherein the microbial indicator cells are resistant to 0.2 ug/ml 5-fluorouridine.

16. The method of claim 1 wherein the microbial indicator cells are further characterized by comprising a defective DNA repair system.

17. The method of claim 1 wherein the microbial indicator cell comprises an error-prone DNA polymerase present on the pKM101 plasmid.

18. The method of claim 1 wherein the microbial indicator cell comprises a mutation which facilitates transport of large compounds in the indicator cells.

* * * * *